(12) United States Patent
Hosoda et al.

(10) Patent No.: US 10,371,614 B2
(45) Date of Patent: Aug. 6, 2019

(54) DIAGNOSTIC SPECTRALLY ENCODED ENDOSCOPY APPARATUSES AND SYSTEMS AND METHODS FOR USE WITH SAME

(71) Applicant: Canon USA, Inc., Melville, NY (US)

(72) Inventors: Masaki Hosoda, Kawasaki (JP); Haruo Nakaji, Kawasaki (JP); Zhuo Wang, Santa Clara, CA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 15/800,780

(22) Filed: Nov. 1, 2017

(65) Prior Publication Data

US 2018/0120212 A1 May 3, 2018

Related U.S. Application Data

(60) Provisional application No. 62/417,084, filed on Nov. 3, 2016.

(51) Int. Cl.
*A61B 1/00* (2006.01)
*A61B 1/04* (2006.01)
(Continued)

(52) U.S. Cl.
CPC .......... *G01N 11/00* (2013.01); *A61B 1/00009* (2013.01); *A61B 1/00147* (2013.01);
(Continued)

(58) Field of Classification Search
None
See application file for complete search history.

(56) References Cited

U.S. PATENT DOCUMENTS

| 3,976,360 A | 8/1976 | Schroder |
| 4,074,306 A | 2/1978 | Kakinuma et al. |

(Continued)

FOREIGN PATENT DOCUMENTS

| WO | 2014031748 A1 | 2/2014 |
| WO | 2014104405 A1 | 7/2014 |

(Continued)

OTHER PUBLICATIONS

Barlev, O., et al., "Design and experimental investigation of highly efficient resonance-domain diffraction gratings in the visible spectral region", Applied Optics, Dec. 1, 2012, pp. 8074-8080, vol. 51, No. 34.

(Continued)

*Primary Examiner* — Shawn Decenzo
(74) *Attorney, Agent, or Firm* — Canon U.S.A., Inc. I.P. Division

(57) ABSTRACT

One or more spectrally encoded endoscopy (SEE) devices, systems, methods and storage mediums for characterizing, examining and/or diagnosing, and/or measuring viscosity of, a sample or object using speckle detection are provided. Examples of such applications include imaging, evaluating and diagnosing biological objects, such as, but not limited to, for Gastro-intestinal, cardio and/or ophthalmic applications, and being obtained via one or more optical instruments. Preferably, the SEE devices, systems methods and storage mediums include or involve speckle intensity autocorrelation function(s). One or more embodiments involve a serial time-encoded 2D imaging system with speckle detection to reconstruct images, store reconstructed images of the sample or object, and/or measure viscosity of the sample or object.

20 Claims, 20 Drawing Sheets

(51) Int. Cl.
*A61B 1/07* (2006.01)
*A61B 5/00* (2006.01)
*G01N 11/00* (2006.01)

(52) U.S. Cl.
CPC ............ *A61B 1/00172* (2013.01); *A61B 1/04* (2013.01); *A61B 1/07* (2013.01); *A61B 5/0062* (2013.01); *A61B 5/0075* (2013.01); *A61B 5/0084* (2013.01); *G01N 2011/006* (2013.01)

(56) References Cited

U.S. PATENT DOCUMENTS

| | | | |
|---|---|---|---|
| 4,264,127 | A | 4/1981 | Schumacher et al. |
| 5,279,280 | A | 1/1994 | Bacich et al. |
| 5,565,983 | A | 10/1996 | Barnard |
| 5,719,399 | A | 2/1998 | Alfano et al. |
| 5,909,529 | A | 6/1999 | Bhagavatula |
| 6,341,036 | B1 | 1/2002 | Tearney et al. |
| 6,485,413 | B1 | 11/2002 | Boppart et al. |
| 6,661,513 | B1 | 12/2003 | Granger |
| 6,831,781 | B2 | 12/2004 | Tearney et al. |
| 6,858,859 | B2 | 2/2005 | Kusunose |
| 7,003,196 | B2 | 2/2006 | Ghiron |
| 7,342,659 | B2 | 3/2008 | Horn et al. |
| 7,355,716 | B2 | 4/2008 | de Boer et al. |
| 7,448,995 | B2 | 11/2008 | Wiklof et al. |
| 7,796,270 | B2 | 9/2010 | Yelin et al. |
| 7,809,225 | B2 * | 10/2010 | Bouma ............. G02B 6/02042 385/123 |
| 7,843,572 | B2 | 11/2010 | Tearney et al. |
| 7,859,679 | B2 | 12/2010 | Bouma et al. |
| 8,045,177 | B2 * | 10/2011 | Tearney ................. A61B 1/227 356/502 |
| 8,145,018 | B2 | 3/2012 | Shishkov et al. |
| 8,203,708 | B2 | 6/2012 | Lee et al. |
| 8,289,522 | B2 | 10/2012 | Tearney et al. |
| 8,570,527 | B2 | 10/2013 | Milner et al. |
| 8,712,506 | B2 | 4/2014 | Courtney et al. |
| 8,780,176 | B2 | 7/2014 | Yelin |
| 8,804,133 | B2 | 8/2014 | Yelin et al. |
| 8,812,087 | B2 | 8/2014 | Yelin et al. |
| 8,818,149 | B2 | 8/2014 | Shishkov et al. |
| 8,838,213 | B2 * | 9/2014 | Tearney ................. A61B 18/22 600/478 |
| 9,057,594 | B2 | 6/2015 | Kang et al. |
| 9,226,979 | B2 | 1/2016 | Hashimshony |
| 9,254,089 | B2 * | 2/2016 | Tearney ............. A61B 5/0062 |
| 9,295,391 | B1 * | 3/2016 | Tearney ................. A61B 1/07 |
| 9,351,642 | B2 * | 5/2016 | Nadkarni ............. A61B 5/0059 |
| 9,557,154 | B2 * | 1/2017 | Tearney ............. A61B 5/0066 |
| 2002/0114566 | A1 | 8/2002 | Fairchild et al. |
| 2002/0145815 | A1 | 10/2002 | Moriyama et al. |
| 2003/0142934 | A1 | 7/2003 | Pan et al. |
| 2004/0147810 | A1 | 7/2004 | Mizuno |
| 2005/0155704 | A1 | 7/2005 | Yokajty et al. |
| 2007/0188855 | A1 | 8/2007 | Shishkov et al. |
| 2007/0233396 | A1 | 10/2007 | Tearney et al. |
| 2007/0276187 | A1 | 11/2007 | Wiklof et al. |
| 2008/0013960 | A1 | 1/2008 | Tearney et al. |
| 2008/0097225 | A1 | 4/2008 | Tearney et al. |
| 2009/0141360 | A1 | 6/2009 | Koyama |
| 2009/0153932 | A1 | 6/2009 | Davis et al. |
| 2009/0209950 | A1 | 8/2009 | Starksen |
| 2010/0210937 | A1 | 8/2010 | Tearney et al. |
| 2010/0317975 | A1 * | 12/2010 | Yelin .................... A61B 5/0084 600/476 |
| 2011/0237892 | A1 | 9/2011 | Tearney et al. |
| 2011/0275899 | A1 | 11/2011 | Tearney et al. |
| 2012/0112094 | A1 | 5/2012 | Kao et al. |
| 2012/0190928 | A1 * | 7/2012 | Boudoux ............. A61B 1/0017 600/166 |
| 2012/0212595 | A1 * | 8/2012 | Parmar ................ A61B 5/0062 348/68 |
| 2013/0012771 | A1 | 1/2013 | Robertson |
| 2014/0276108 | A1 | 9/2014 | Vertikov |
| 2014/0285878 | A1 | 9/2014 | Escuti et al. |
| 2014/0378846 | A1 * | 12/2014 | Hosoda ................ A61B 5/6876 600/478 |
| 2015/0045622 | A1 | 2/2015 | Shishkov et al. |
| 2015/0080719 | A1 * | 3/2015 | Wheatley ................. A61B 1/07 600/429 |
| 2015/0131098 | A1 | 5/2015 | Yang et al. |
| 2015/0335248 | A1 | 11/2015 | Huang et al. |
| 2015/0374246 | A1 * | 12/2015 | Yelin .................... A61B 5/0261 600/479 |
| 2016/0341951 | A1 * | 11/2016 | Tearney ............. A61B 1/00096 |
| 2017/0176736 | A1 | 6/2017 | Yamamoto et al. |

FOREIGN PATENT DOCUMENTS

| | | |
|---|---|---|
| WO | 2015116939 A1 | 8/2015 |
| WO | 2015116951 A2 | 8/2015 |
| WO | 2015116974 A1 | 8/2015 |
| WO | 2017/024145 A1 | 2/2017 |
| WO | 2017/106347 A1 | 6/2017 |
| WO | 2017/117203 A1 | 7/2017 |
| WO | 2017/139657 A1 | 8/2017 |

OTHER PUBLICATIONS

Zeidan, A et al. "Miniature forward-viewing spectrally encoded endoscopic probe", Optics Letters, Aug. 15, 2014, pp. 4871-4874, vol. 39, Issue 16.

Pitris, C. et al., "A GRISM-based probe for spectrally encoded confocal microscopy" Optics Express, Jan. 27, 2003, pp. 120-124, vol. 11, No. 2.

Yelin, D., et al., "Three-dimensional miniature endoscopy", Nature, Oct. 19, 2006, p. 765, vol. 443.

Kang, D., et al., "Minature grating for spectrally-encoded endoscopy", Lab Chip, 2013, pp. 1810-1816, vol. 13.

Kang, D., et al., "Spectrally-encoded color imaging", Optics Express, Aug. 17, 2009, pp. 15239-15247, vol. 17, No. 17.

Moharam, M.G., et al, "Formlation for stable and efficient implementation of the rigorous coupled-wave analysis of binary gratings", J. Opt. Soc. Am. A, May 1995, pp. 1068-1076, vol. 12, No. 5.

Yun, et al., "High-speed spectral-domain optical coherence tomography at 1.3 μm wavelength", Opt Express, Dec. 29, 2003, pp. 3598-3604, No. 11, vol. 26.

Tearney, G.J., et al., "Spectrally encoded miniature endoscopy", Optics Letters, Mar. 15, 2002, pp. 412-414, vol. 27, No. 6.

Bai, B., et al. "Optimization of nonbinary slanted surface-relief gratings as high-efficiency broadband couplers for light guides", Applied Optics, Oct. 1, 2010, pp. 5454-5464, vol. 49, No. 28.

* cited by examiner

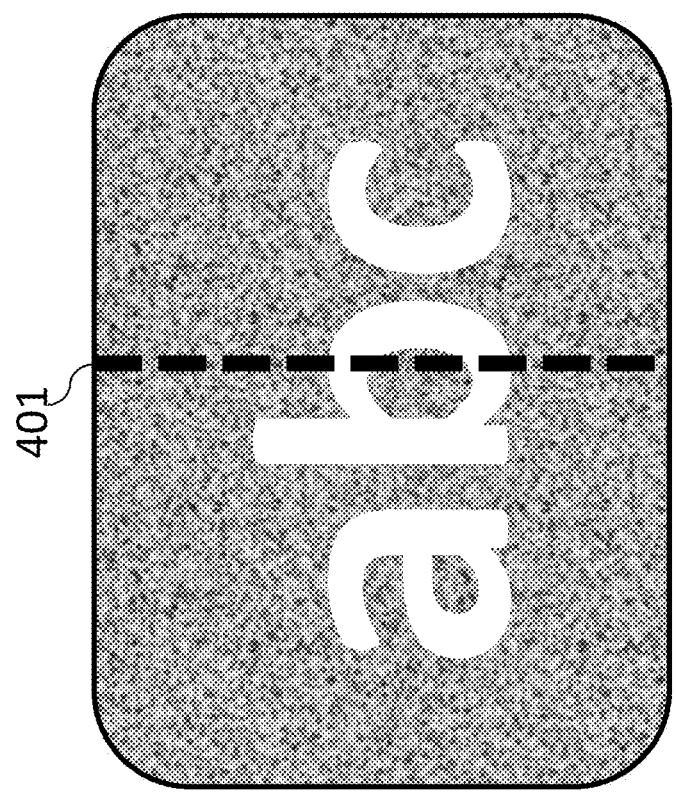

DIAGNOSTIC SPECTRALLY ENCODED ENDOSCOPY APPARATUSES AND SYSTEMS AND METHODS FOR USE WITH SAME

CROSS-REFERENCE TO RELATED APPLICATION(S)

This application claims priority to U.S. Provisional Application Ser. No. 62/417,084 filed 3 Nov. 2016, the content of which is incorporated herein by reference in its entirety.

FIELD OF THE INVENTION

The present disclosure relates generally to the field of optical imaging and more particularly to spectrally encoded endoscopy (SEE) apparatuses and systems, and methods and storage mediums for use with same. Examples of SEE applications include imaging, evaluating and characterizing/identifying biological objects or tissue, such as, but not limited to, for gastro-intestinal, cardio and/or ophthalmic applications.

BACKGROUND OF THE INVENTION

Spectrally encoded endoscope (SEE) is an endoscope technology which uses a broadband light source, a rotating grating and a spectroscopic detector to encode spatial information on a sample. When illuminating light to the sample, the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained.

In the field of medical diagnoses, a thin (<0.5 mm) probe is highly expected for imaging organs or tissues located in deep with less interventions. A SEE probe has tremendous potential to provide high resolution imaging through small optical fibers.

A basic SEE system can only provide morphological images, and then physicians may not be able to obtain any tissue information other than images. For example, a Doppler SEE can provide flow velocity information with additional heterodyne interferometric equipment for broadband wavelength. The Doppler measurement has an advantage for measuring localized flow velocities, such as identification of blood flow. However, the main problem of using the Doppler measurement is that it requires continuous particle flow in one direction perpendicular to the optical axis. When light scattering particles in tissue moves randomly, which is seen in any tissues, the accuracy of the Doppler measurement is essentially dropped. Therefore, using the Doppler measurement is difficult for physicians to characterize tissue type.

Additionally, those skilled in the art try to remove, or avoid the use of, speckle detection when evaluating or characterizing tissue due to noise and/or inefficiencies related to speckle detection.

Accordingly, it would be desirable to provide at least one SEE technique, storage medium and/or apparatus or system for use in at least one optical device, assembly or system to achieve efficient characterization and/or identification of biological object(s) or tissue, especially in a way that reduces or minimizes cost of manufacture and maintenance.

SUMMARY OF THE INVENTION

Accordingly, it is a broad object of the present disclosure to provide SEE apparatuses and systems, and methods and storage mediums for use with same.

In accordance with one or more embodiments of the present disclosure, SEE apparatuses and systems, and methods and storage mediums may operate to characterize tissue type in addition to providing a morphological image to help an operator's diagnostic decision based on quantitative tissue information.

A laser source generates broadband laser lights. The broadband laser lights from a laser source may be coupled with an illumination fiber (IF) and delivered to a diffraction grating (DG), which is disposed on the tip of the IF and can separate different wavelengths in a line with high resolution. The separated illumination lights are emitted from the surface of the grating to illuminate an object and reflected lights (returned lights) from an object pass through the grating again and delivered to a spectrometer by a detection fiber (DF). The SEE probe may include the illumination fiber, the diffraction grating and the detection fiber, and they are housed by a metal or plastic tithe to enhance its robustness for rotational motions and external stress by insertion. The SEE probe has a lens at the distal end of the probe, which is located after diffraction grating, or between the diffraction grating and the illumination fiber, or between the diffraction grating and the detection fiber. The SEE probe is incorporated with a motor (M) at the proximal side, which enable the SEE probe scans in horizontal direction with periodical arc motion. The motor can be a rotational motor to achieve circumferential viewing. The detection fiber is coupled with a spectrometer including a diffraction grating and a line detector. A console controls motions of the motor, acquires intensity data from the detector in the spectrometer, and display the scanned image. In one or more embodiments, step grating applications may be incorporated, such as those disclosed in U.S. Provisional Patent Application No. 62/363,089, filed Jul. 15, 2016, published as U.S. Pat. Pub. No. 2018/0017806 on Jan. 18, 2018, and issued as U.S. Pat. No. 10,234,694 on Mar. 19, 2019, which is incorporated by reference herein in its entirety.

In accordance with at least one aspect of the present disclosure, tissue characterization or identification may be added to a SEE apparatus or system. At least one embodiment of the present disclosure measures tissue viscosity for identifying tissue type, which is obtained by speckle intensity autocorrelation, to efficiently identify the tissue and maintain or improve accuracy in identifying the tissue. One of the advantages of the measurement using speckle intensity autocorrelation compared to the aforementioned Doppler measurement is that using speckle intensity autocorrelation can detect random motions of scattering particles in tissue, which relates to viscosity of the tissue. Measuring viscosity can help physicians identify tissue type. Indeed, by way of a couple of examples, one or more embodiments of the present disclosure may include a SEE probe used with speckle detection, and may include a SEE probe used with speckle detection where tissue viscosity may be measured in addition to obtaining the SEE image. Thus, in one or more embodiments, intravascular laser speckle imaging (ILSI), or laser speckle imaging (LSI), may be employed to obtain viscosity measurements, and may be employed with a SEE probe.

In accordance with one or more embodiments of the present disclosure, SEE apparatuses and systems, and methods and storage mediums may operate to characterize biological objects other than tissue. For example, the characterization may be of a biological fluid such as blood or mucus.

At least two embodiments of the present disclosure involve characterizing tissue type using at least one embodiment of a SEE system with a side viewing probe and a forward viewing probe, respectively.

In accordance with one or more aspects of the present disclosure, at least one embodiment of a SEE apparatus or system may relate to forward and side views or imaging. Additionally or alternatively, one or more embodiments of a SEE apparatus or system may relate to using a photo diode and for serial time-encoded 2D imaging. At least one embodiment may obtain a color SEE image (either with a front view and/or a side view).

In accordance with one or more aspects of the present disclosure, at least one embodiment of an apparatus for characterizing or identifying a sample includes: an interface including a light guiding component, and a motor; a spectral encoder including a light focusing component and a light dispersive component; and a speckle detector including a motion control component that operates to change a speed of the motor, and at least one processor that operates to calculate a speckle intensity autocorrelation function and/or process or perform laser speckle imaging (LSI).

In accordance with one or more aspects of the present disclosure, at least another embodiment of an apparatus for identifying sample type of a sample includes: a Spectrally Encoded Endoscopy ("SEE") probe including at least a grating and one or more optical fibers; a spectrometer; a detector that operates to acquire one or more intensities; a motor; a motion control component that operates to change a speed of the motor; and at least one processor that operates to calculate a speckle intensity autocorrelation function and/or process or perform laser speckle imaging (LSI). The apparatus may further include at least one of: a light source; a spacer element disposed at a distal end of the SEE probe such that the spacer element and the grating are adjacent and/or connected; and a sheath housing the SEE probe, wherein the motor includes, is connected to or is a rotary junction that operates to rotate the SEE probe. The apparatus may be a forward-viewing SEE apparatus or a side-viewing SEE apparatus. The motor may be a stepping motor or a servo motor. The apparatus may include a memory coupled to the at least one processor, the memory operating to store a look-up table including β values and decay times calculated by speckle intensity autocorrelation functions, and including the sample type. The one or more optical fibers may include; (i) one or more illumination fibers that operate to send light from a light source through the motor and to the grating to illuminate the sample with light; and (ii) one or more detection fibers that operate to receive light reflected from the sample and that passes back through the grating and into the one or more detection fibers.

In one or more embodiments, at least one of the following may occur: (i) the motion control component stops the motor while the detector acquires the one or more intensities; and (ii) the motion control component changes the speed of the motor while the detector acquires the one or more intensities. The motion control component may stop the motor at different motor positions at least two times, while the detector may acquire the one or more intensities, or may change the speed of the motor at different motor positions at least two times, when the detector acquires intensities. The motion control component may stop the motor at each motor position in successive scanning, while the detector acquires the one or more intensities.

The apparatus may include a display or screen that operates to display a user interface via which an operator or user of the apparatus selections one or more positions, one or more lines or one or more regions of interest from which to obtain the one or more intensities. The display or screen may further operate to display overlapped images of morphological feature(s) and viscosity or the sample type of the sample being characterized, diagnosed and/or examined.

The apparatus may include a photodiode optically connected to the grating and connected to the at least one processor, and the photodiode operates to detect one or more time varying speckle intensities separated from the spectrometer. In one or more embodiments, at least one of the following may occur or be included: a whole range of wavelength or windowed range of wavelength is averaged when the photodiode obtains intensity data; the photodiode is connected to at least one of the one or more optical fibers through a fiber coupler; the stored intensity data obtained by the photodiode is solely used for calculating the speckle intensity autocorrelation function, so that the at least one processor can separate the SEE imaging and sample characterization to stabilize the apparatus; and the speckle intensity autocorrelation function or functions acquired in each scanning line are more distinguishable for sample characterization, because achievable Hz by the photodiode is higher than when using the detector.

In accordance with another aspect of the present disclosure, at least one embodiment of a serial time-encoded 2D imaging system with speckle detection may include: an interface including a light guiding component; a deflecting section that operates to receive light from the light guiding component; a two-dimensional (2D) disperser that operates to: (i) receive light from the deflecting section, (ii) to divide incident light into 2D illumination lights with different wavelength at each 2D position to illuminate a sample, and (iii) receive light reflected from the sample, combine the reflected light and pass the light to the deflecting section; a dispersion compensation fiber that operates to: (i) receive the reflected, combined light from the 2D disperser via the deflecting section, and (ii) make chromatic dispersion and intensity data reflected by the sample dispersed in a time domain; a photodiode connected to the dispersion compensation fiber, the photodiode operating to detect time delay such that intensities of each wavelength associating or associated with a position at the sample are distinguishable based on the time delay; and at least one processor, which is connected to the photodiode, that operates to store intensity data in a memory and reconstruct images and/or store reconstructed images of the sample. The deflecting section may be a circulator that operates to deflect light from a light source to a SEE probe, and then send light received from the SEE probe toward the photodiode or another detector. The system may calculate viscosity of the sample using accumulated speckle fluctuations.

In accordance with yet a further aspect of the present disclosure, at least one embodiment of a system for characterizing a sample may include: an apparatus for characterizing the sample, the apparatus including: (i) an interface including a light guiding component, and a motor; (ii) a spectral encoder including a light focusing component and a light dispersive component; and (iii) a speckle detector including a motion control component that operates to change a speed of the motor, and at least one processor that operates to calculate a speckle intensity autocorrelation function and/or process or perform laser speckle imaging (LSI); a light source that operates to send light to the light guiding component of the apparatus for characterizing the sample; a rotary junction connected to or with the interface of the apparatus; and a spectrometer including at least one detector. The system may include a sheath having a plurality of tendons therein, the plurality of tendons operating to control motion of the sheath. The plurality of tendons may include four tendons, where two of the four tendons control up-down and down-up movement of the sheath and the other two of the four tendons control left-right and right-left movement of the sheath.

In accordance with yet a further aspect of the present disclosure, at least one embodiment of a method for characterizing a sample with speckle detection using a Spectrally Encoded Endoscopy ("SEE") system may include: forming a SEE image of the sample; designating at least a partial region or line in the SEE image; calculating a speckle intensity autocorrelation function to determine a sample type in the designated region or line and/or performing or processing laser speckle imaging (LSI); and causing a display of the SEE system to display the sample type information together with the SEE image. The forming of the SEE image step may further include: generating a light or broadband laser in a light or laser source; delivering the light or the broadband laser with an illumination fiber to a grating; emitting the light or the broadband laser diffused via the grating disposed on a tip of the illumination fiber; rotating the illumination fiber while emitting the light or the broadband laser; detecting, with a detection fiber, a returned light of the emitted light or the emitted broadband laser returned from the sample, while the illumination fiber is rotated; and obtaining spectrally-encoded signals from the detected, returned light by a spectrometer, to form the SEE image. The method may further include: setting sample information; designating one or more imaging conditions; starting the imaging or the formation of the SEE image and/or starting reconstruction or formation of the SEE image or images; displaying the scanned images; determining whether to display the sample type; if it is determined to not display the sample type, then keep displaying the scanned images, or, if it is determined to display the sample type, then determine whether to display a whole area, a line or a region of interest (ROI); if it is determined to display a whole area, then step-scan stop positions when acquiring intensity and proceed to calculating a g2(t) function to determine the sample type, or, if it is determined to display a line or an ROI, then display a graphical user interface (GUI) for letting a user or operator select a line or an ROI, send a control signal to change a scanning speed when acquiring intensity and then proceed to the calculating of the g2(t) function to determine the sample type; sending a control signal to change a scanning speed when acquiring intensity; calculating a g2(t) function to determine the sample type; displaying overlapped image and the sample type; and determining whether to end the characterization or not. The method may further include: setting sample information; designating one or more imaging conditions; starting the imaging or the formation of the SEE image and/or starting reconstruction or formation of the SEE image or images; coordinating intensities to construct a SEE image; calculating a g2(t) function to determine the sample type; displaying the sample type on a center or other predetermined location of a scanned image; and determining whether to change the line or ROI or not. In one or more embodiments, the method may further include: if it is determined to change the line or ROI, then adjust a measuring position toward the center of the image and then determine whether to end the characterization, or if it is determined to not change the line or ROI, then keep displaying the scanned image and the sample type and repeat the determination step as to whether to change the line or ROI or not. The method may further include calculating viscosity of the sample using accumulated speckle fluctuations.

In accordance with yet another aspect of the present disclosure, at least one embodiment of a computer-readable storage medium storing a program that operates to cause one or more processors to execute a method for characterizing a sample with speckle detection, the method comprising: forming a SEE image of the sample; designating at least a partial region or line in the SEE image; calculating a speckle intensity autocorrelation function to determine a sample type in the designated region or line and/or performing or processing laser speckle imaging (LSI); and causing a display of the SEE system to display the sample type information together with the SEE image.

One or more embodiments of the present disclosure may be used in clinical application(s), such as, but not limited to, balloon sinuplasty, sinus stenting, other sinus treatment(s), arthroscopy, use for/in the lacrimal duct, sialo endoscopy, ear research, veterinary use and research, etc. For example, at least one embodiment may be used for balloon sinuplasty to achieve success because balloon sinuplasty is a technique that relates to moving viscous mucus to a side of a passage using a balloon. As such, it is useful to be able to measure viscosity in such a situation, in any other of the aforementioned application(s), or any other application(s) that would be appreciated by those skilled in the art.

In accordance with at least another aspect of the present disclosure, the SEE technique(s) discussed herein may be employed to reduce the cost of at least one of manufacture and maintenance of SEE devices, systems and storage mediums by reducing or minimizing a number of optical components in an interference optical system, such as an interferometer.

In accordance with at least a further aspect of the present disclosure, the SEE technique(s) discussed herein may be used with or without speckle detection in or used with an interference optical system, such as an interferometer.

According to other aspects of the present disclosure, one or more additional devices, one or more systems, one or more methods and one or more storage mediums using SEE technique(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIG. 4 is a diagram showing at least one embodiment of a user interface for selecting a line for measuring or characterizing tissue type using a SEE apparatus or system in accordance with one or more aspects of the present disclosure;

DETAILED DESCRIPTION OF THE PRESENT INVENTION

One or more devices, optical systems, methods and storage mediums for characterizing tissue using a SEE technique and/or speckle detection are disclosed herein. In accordance with at least one aspect of the present disclosure, one or more devices, optical systems, methods and storage mediums discussed herein use a SEE technique with speckle detection or employ a serial time-encoded 2D imaging system with speckle detection.

Figure 1:
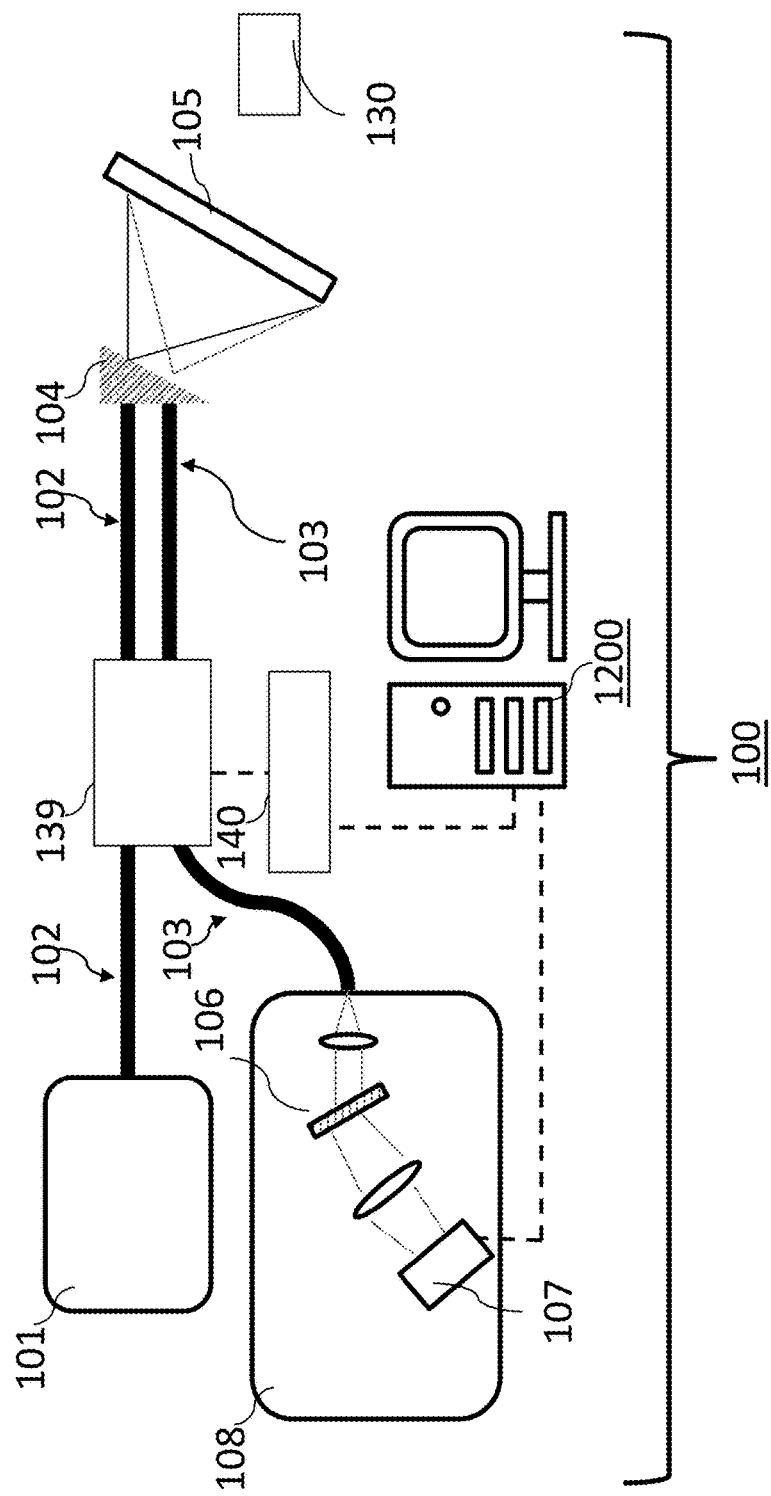
FIG. 1 is a diagram showing an embodiment of a side-viewing SEE system with speckle detection in accordance with one or more aspects of the present disclosure.

Turning now to the details of the figures, FIG. 1 shows an embodiment of a Spectrally Encoded Endoscopy ("SEE") system 100 (also referred to herein as "system 100" or "the system 100") which operates to utilize a SEE technique with speckle detection for optical probe applications in accordance with one or more aspects of the present disclosure. In at least one embodiment, the system 100 comprises a light source 101, an illumination fiber 102, a detection fiber 103, a motor 139, a spectrometer 108, at least one detector 107, a diffraction grating 104 that operates to produce or interact with illumination light 105 and/or light reflected from an object (e.g., object 130), a Motion Control Unit (MCU) 140, and a computer, such as, but not limited to a computer 1200, 1200', that operates to calculate a speckle intensity autocorrelation function. The system 100 may interact with the sample, specimen or object (e.g., object 130) via the illumination light 105 (as schematically shown in FIG. 1). The light source 100 generates broadband laser lights in one or more embodiments. The broadband laser lights from the laser source 100 are coupled with the illumination fiber (IF) 102 and delivered to the diffraction grating (DG) 104, which is disposed on a tip of the IF 102, and, in one or more embodiments, the IF 102 can separate different wavelengths in a line with high resolution. The separated illumination lights (e.g., illumination light 105) are emitted from a surface of the diffraction grating 104 to illuminate the object, and reflected lights (returned lights) from the object pass through the diffraction grating 104 again and are delivered to the spectrometer 108 by the detection fiber (DF) 103. In some embodiments, the reflected lights (returned lights) from the object (e.g., the object 130) are delivered to the spectrometer 108 by the detection fiber (DF) 103 without first passing through the diffraction grating 104.

Figure 11A:
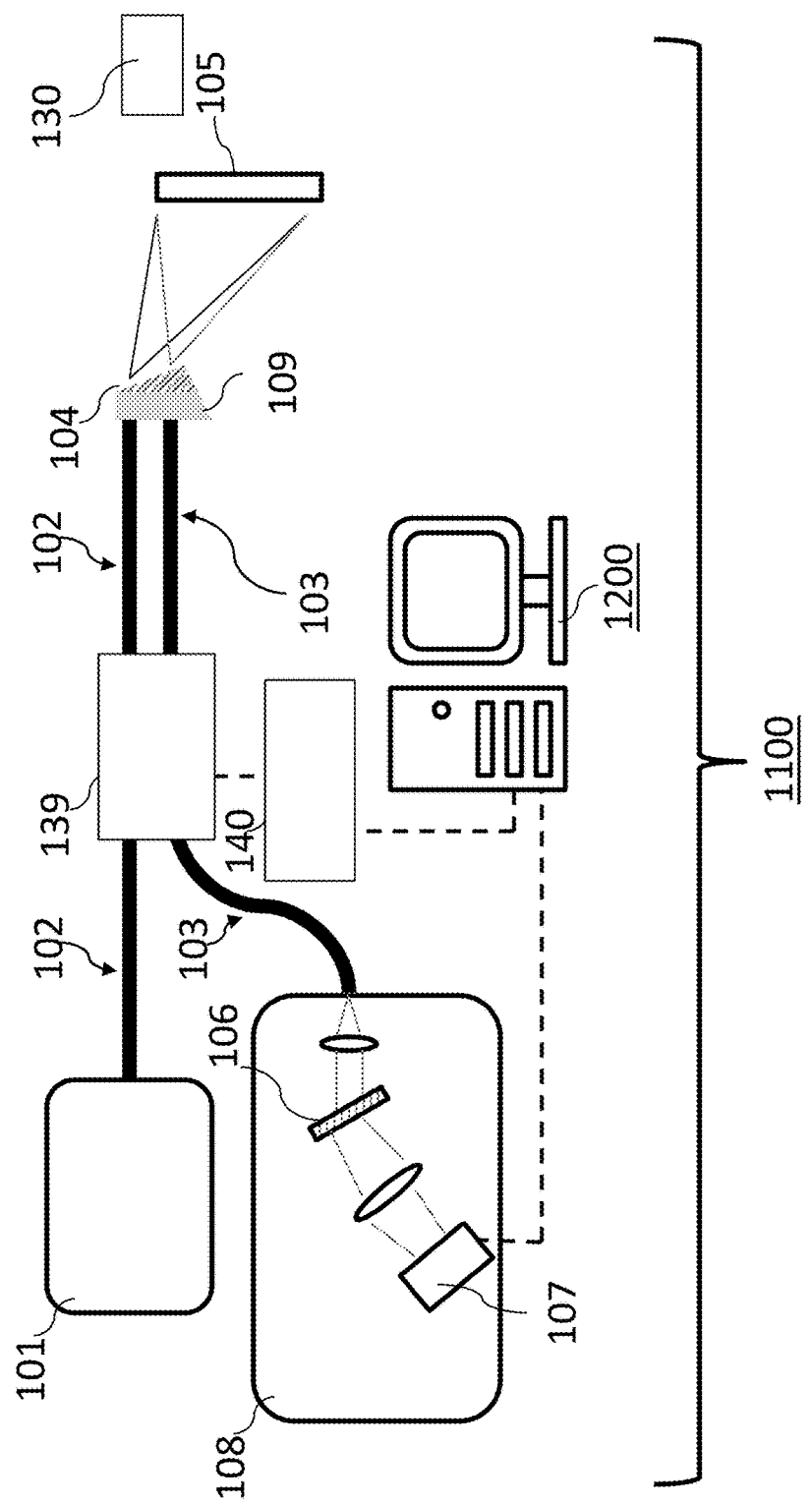
FIG. 11A is a diagram showing an embodiment of a forward-viewing SEE system with speckle detection in accordance with one or more aspects of the present disclosure.
Figure 11B:
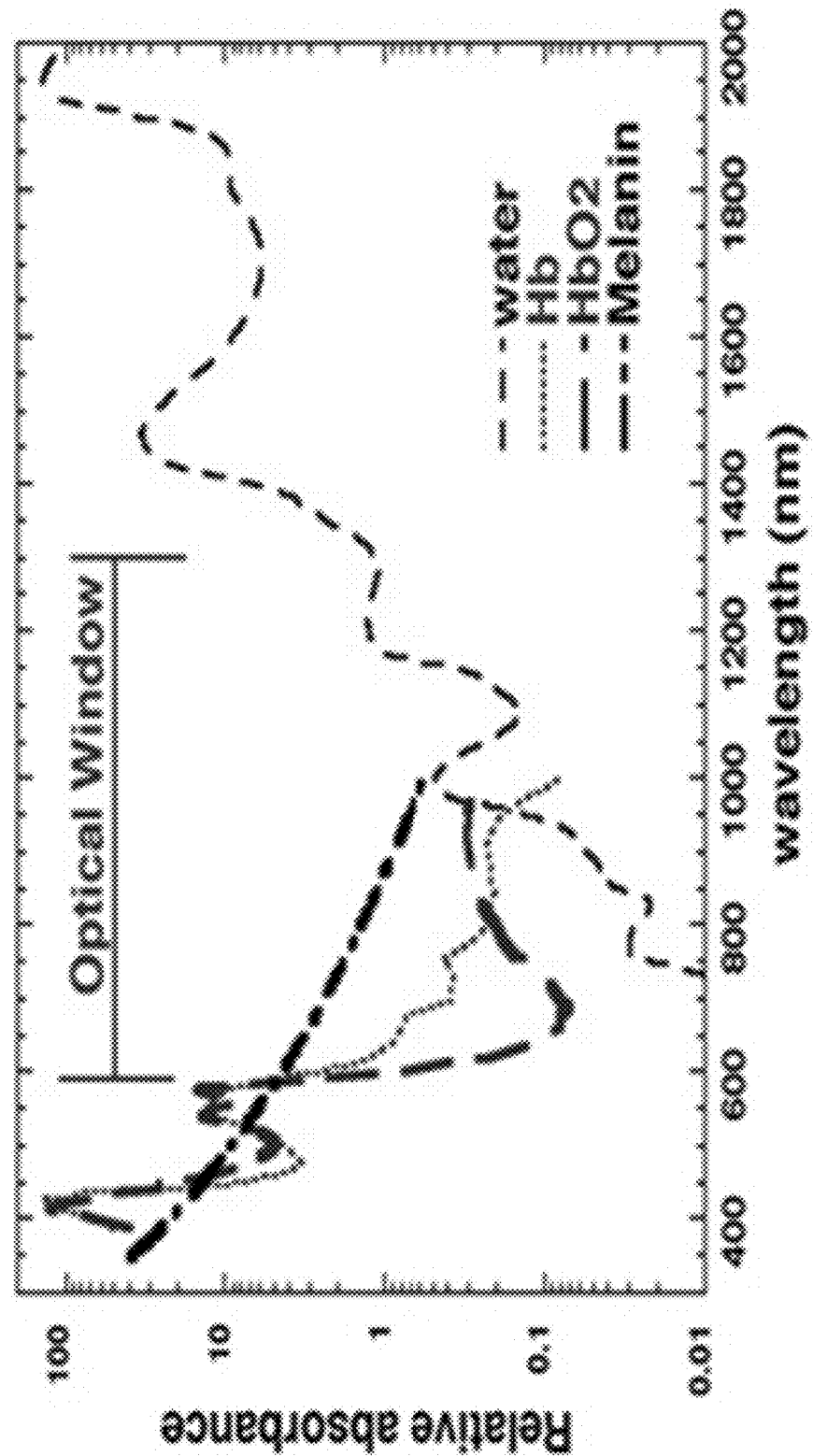
FIG. 11B is a graph illustrating at least one embodiment of dependence between a g2 function and wavelength in accordance with one or more aspects of the present disclosure.

In one or more embodiments, a SEE probe may include the illumination fiber 102, the diffraction grating 104 and the detection fiber 103, and the illumination fiber 102, the detection fiber 103 and the diffraction grating 104 may be housed by a metal or plastic tube to enhance the SEE probe's robustness for rotational motions and external stress by insertion. The SEE probe may further include a lens at the distal end of the probe, which may be located after the diffraction grating 104 (not shown), or between the diffraction grating 104 and the illumination fiber 102 (see e.g., the lens or prism 109 as shown in FIG. 11A and as discussed further below), or between the diffraction grating 104 and the detection fiber 103 (see e.g., the lens or prism 109 as shown in FIG. 11A and as discussed further below). In one or more embodiments, a SEE probe is incorporated with the motor (M) 139 at a proximal side, which enables the SEE probe to scan in a horizontal direction, for example, with a periodical arc motion. In one or more embodiments, the motor (M) 139 may be a rotational motor to achieve, for example, circumferential viewing. In some embodiments, the system 100 includes one or more rotary junctions (not shown) that are configured to rotate the illumination fiber 102 or the illumination fiber 102 and the detection fiber 103. In at least one embodiment (see e.g., FIGS. 1 and 11), the detection fiber 103 may be coupled with the spectrometer 108 including a diffraction grating 106 and the at least one detector 107.

In at least one embodiment, the console 1200, 1200' operates to control motions of the motor (M) 139 via the Motion Control Unit (MCU) 140, acquires intensity data from the at least one detector 107 in the spectrometer 108, and displays the scanned image (e.g., on a monitor or screen such as a display, screen or monitor 1209 as shown in the console 1200 of FIG. 18 and/or the console 1200' of FIG. 19 as further discussed below). In one or more embodiments, the MCU 140 operates to change a speed of the motor 139 and/or to stop the motor 139. The motor 139 may be a stepping or a DC servo motor to control the speed and increase position accuracy.

The output of the one or more components of the system 100 is acquired with the at least one detector 107, e.g., such as, but not limited to, photodiodes, Photomultiplier tube(s) (PMTS), line scan camera(s), or multi-array camera(s). Electrical analog signals obtained from the output of the system 100 and/or the spectrometer thereof are converted to digital signals to be analyzed with a computer, such as, but not limited to, the computer 1200, 1200' (e.g., as shown in FIGS. 1 and 11 discussed further below). In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum. In some embodiments, the at least one detector 107 comprises three detectors configured to detect three different bands of light. In yet other embodiments, the spectrometer 108 is configured to generate three 2D images from three different bands of light (e.g., red, green, and blue) where these three 2D images may be combined to form a single image having color information. In yet other embodiments, multiple spectrometers 108 may be used to generate different 2D images from the three different bands of light.

Figure 2:
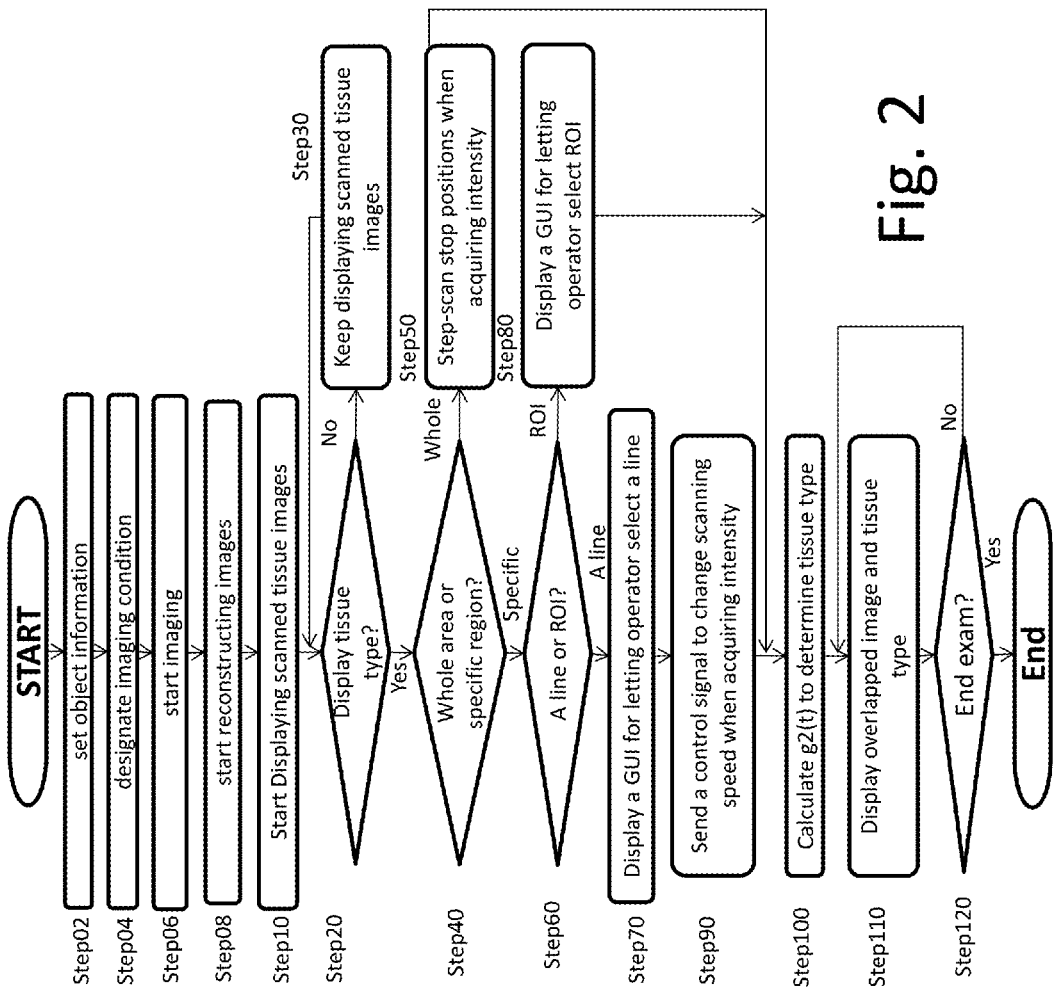
FIG. 2 is a flowchart illustrating at least one embodiment of a method for using or use with a side-viewing SEE system with speckle detection for characterizing tissue in accordance with one or more aspects of the present disclosure.

In accordance with at least one aspect of the present disclosure and as aforementioned, one or more methods for performing tissue characterization when using a SEE system with speckle detection are provided herein. FIG. 2 illustrates a flow chart of at least one embodiment of a method for characterizing tissue using a SEE system (e.g., with the SEE system of FIG. 1). Preferably, the method(s) may include one or more of the following: (i) setting object information (see step 02 in FIG. 2); (ii) designating one or more imaging conditions (see step 04 in FIG. 2); (iii) start imaging (see step 06 in FIG. 2); (iv) start reconstructing images (see step 08 in FIG. 2); (v) start displaying scanned tissue images (see step 10 in FIG. 2); (vi) display tissue type (see step 20 in FIG. 2); (vii) if "NO" in step 20, then keep displaying scanned tissue images and return to step 20 (see step 30 in FIG. 2), or if "YES" in step 20, then determine whether to display a whole area or a specific region (see step 40 in FIG. 2); (viii) if "WHOLE" in step 40, then step-scan stop positions when acquiring intensity and proceed to step 100 (see step 50 in FIG. 2), or if "Specific" in step 40, then determine whether to display a line or a region of interest (ROI) (see step 60 in FIG. 2); (ix) if a "line" in step 60, then display a graphical user interface (GUI) for letting a user or operator select a line (see step 70 in FIG. 2), or if an "ROI" in step 60, then display a GUI for letting the user or operator select an ROI and then proceed to step 100 (see step 80 in FIG. 2); (x) send a control signal to change a scanning speed when acquiring intensity (see step 90 in FIG. 2); (xi) calculate g2(t) to determine tissue type (see step 100 in FIG. 2); (xii) display overlapped image and tissue type (see step 110 in FIG. 2); and (xiii) determine whether to end the exam or evaluation (see step 120 in FIG. 2). If "YES" in step 120, then end the exam or evaluation. If "NO" in step 120, then return to step 110.

In the step 02, the computer, such as the console or computer 1200, 1200', sets object information for an examination with a SEE system, such as the system 100. The object information may include a name, an ID number, an age and a sex. The computer, such as the console or computer 1200, 1200', relates an examination ID with the set object information. The computer, such as the console or computer 1200, 1200', may receive the object information from the Hospital Information. System (HIS) or other system via a network interface (see e.g., communication interface 1205 and network 1206 as shown in FIG. 18 or Network I/F 1212 as shown in FIG. 19), or the computer, such as the console or computer 1200, 1200', may obtain the object information using the operation input from a mouse or keyboard (see e.g., the keyboard 1210 as shown in FIG. 18 or the mouse 1211 and/or keyboard 1210 as shown in FIG. 19).

In the step 04, the computer, such as the console or computer 1200, 1200', designates a set of imaging conditions for the examination. In at least one embodiment, a set of imaging conditions includes a condition of the wavelength of the illumination light (e.g., the illumination light 105), a condition of a frame rate of the image, a condition of a size of an imaging region, a condition of a region for which viscosity is to be measured. A set of imaging conditions may include the image processing parameters for reconstructing the image and for displaying the image. The computer, such as the console or computer 1200, 1200', may receive a set of imaging conditions from the Hospital Information System (HIS) or other system via network interface (see e.g., communication interface 1205 and network 1206 as shown in FIG. 18 or Network I/F 1212 as shown in FIG. 19), or the computer, such as the console or computer 1200, 1200', may obtain a set of imaging conditions using the operation input from the mouse or keyboard (see e.g., the keyboard 1210 as shown in FIG. 18 or the mouse 1211 and/or keyboard 1210 as shown in FIG. 19).

In the step 06, the computer, such as the console or computer 1200, 1200', transmits a control signal to start imaging. The computer, such as the console or computer 1200, 1200', may transmit a control signal to the MCU 140 to start rotating the motor 139, transmit a control signal to the light source 101 to start emitting the laser/light, and transmit a control signal to the spectrometer 108 to start operation thereof. In at least one embodiment to reduce a time to wait for the light or laser light to be stable, and for the motor 139 to rotate stably, control signals to start the operations of the light source 101 and the motor 139 are transmitted before or at the step 04 or step 02. The control signal to start the operation of the light source 101 may be transmitted before the control signal to start the operation of the motor 139 is transmitted.

In the step 08, the computer, such as the console or computer 1200, 1200', starts to reconstruct the scanned tissue images using the intensity data from the spectrometer 108. Because detection fibers 103 continuously receives the signal from lights returned from the sample (e.g., object 130), the computer, such as the console or computer 1200, 1200', continuously reconstruct the images, at the frame rate set as one of the imaging conditions in step 04.

Figure 18:
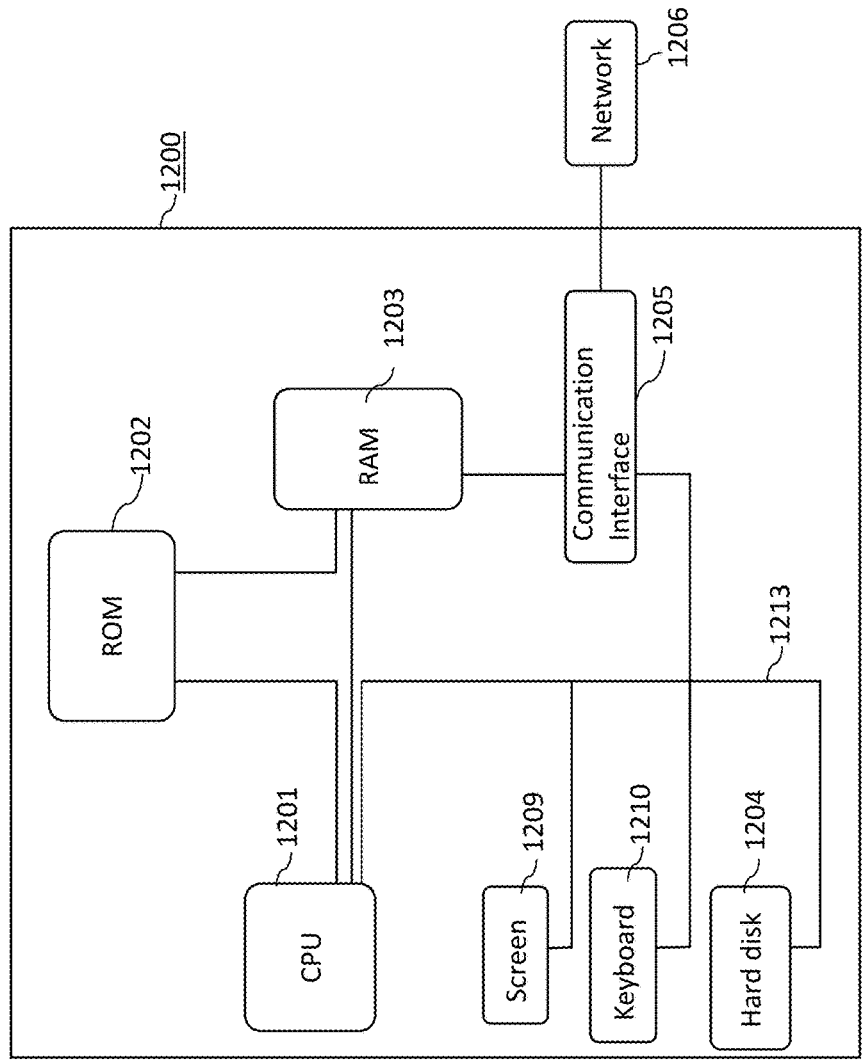
FIG. 18 shows a schematic diagram of an embodiment of a computer that may be used with one or more embodiments of a SEE apparatus or system or an imaging system in accordance with one or more aspects of the present disclosure.
Figure 19:
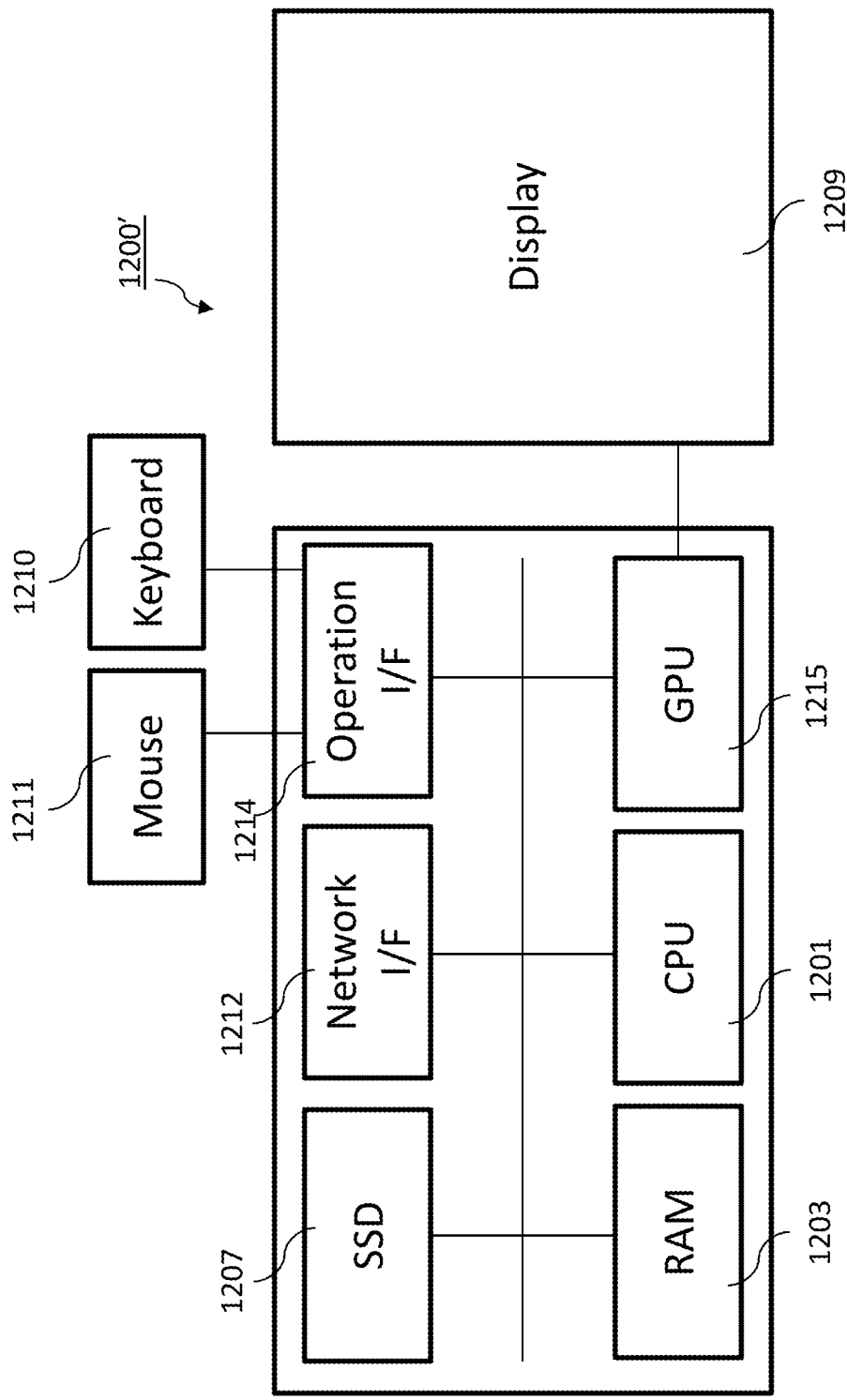
FIG. 19 shows a schematic diagram of another embodiment of a computer that may be used with one or more embodiments of a SEE apparatus or system or an imaging system in accordance with one or more aspects of the present disclosure.

In the step 10, the computer, such as the console or computer 1200, 1200', in the SEE system (e.g., the system 100, the system 1100 as discussed below, etc.) causes the monitor (e.g., the screen 1209 as shown in FIG. 18, the display 1209 as shown in FIG. 19, etc.) to display the scanned tissue images. Based on the displayed tissue images, an operator can decide if he or she needs to know a tissue type. At clinically interesting tissue positions or at predetermined tissue positions, an operator or user can change a measurement mode from a normal imaging mode to a diagnostic mode.

The computer, such as the console or computer 1200, 1200', determines if the tissue type should be displayed based on an operation input from an operation unit (e.g., such as, but not limited to, a mouse device 1211, a keyboard 1210, a touch panel device, etc.) in the step 20. If "Yes" in the step 20, then the method proceeds to step 40. If "No" in step 20, then the method proceeds to step 30, and the computer, such as the console or computer 1200, 1200', in the SEE system (e.g., the system 100) causes the display (e.g., the display or screen 1209) to keep displaying the scanned tissue image.

Then the operator or user chooses if he or she needs to know tissue type in the whole area or the specific region in the image. In the step 40, the computer, such as the console or computer 1200, 1200', receives an operation input corresponding to the operator's choice to determine if the tissue type in the whole area or the specific region in the image should be displayed. If it is determined that a "Specific" region is to be displayed in step 40, then the method proceeds to the step 60. If it is determined that a "Whole" area is to be displayed in step 40, then the method proceeds to the step 50.

Figure 3:
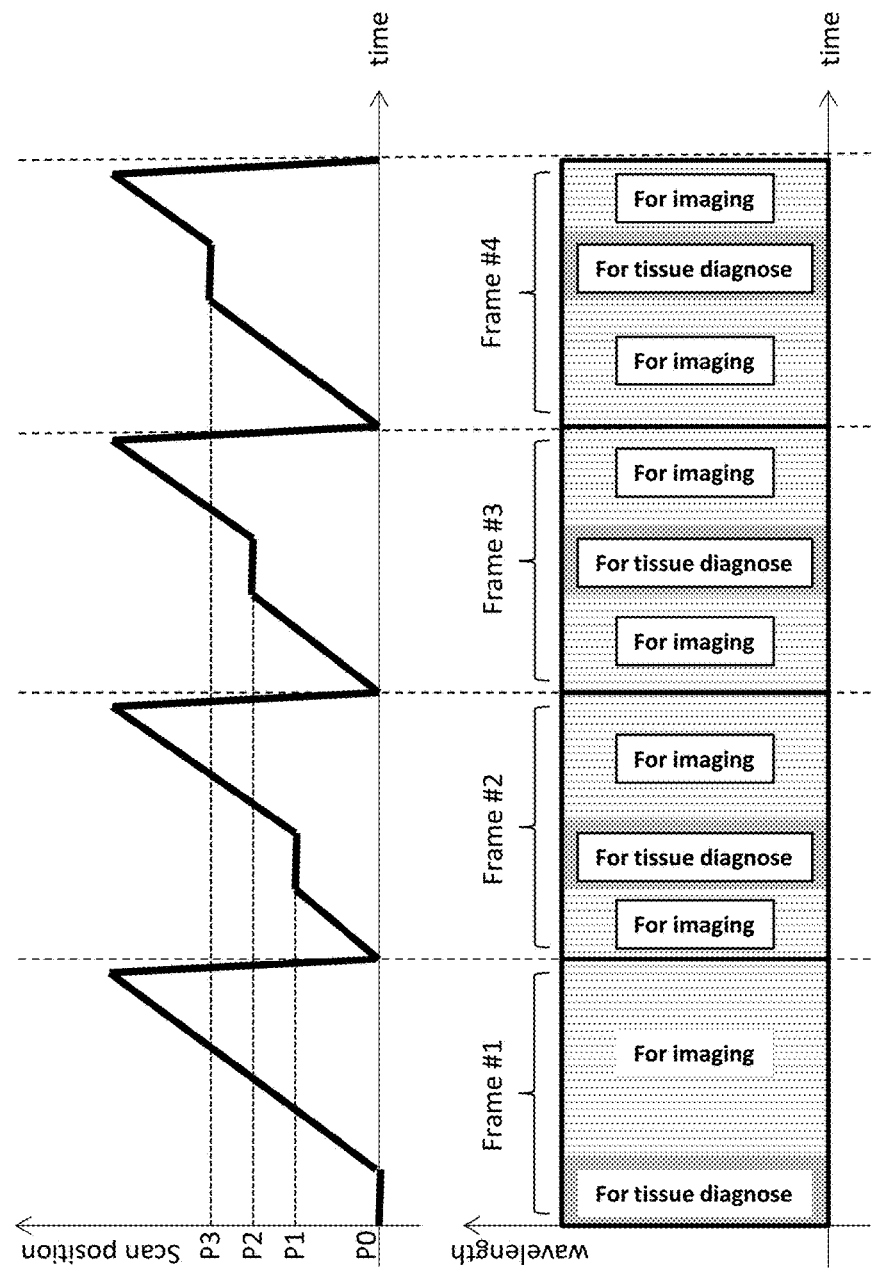
FIG. 3 illustrates top and bottom diagrams showing at least one embodiment of an intensity acquisition sequence when using a SEE apparatus or system in accordance with one or more aspects of the present disclosure.

In the step 50, the computer, such as the console or computer 1200, 1200', transmits a control signal to the MCU 140 to control a motor (e.g., the motor 139) for step-scanning the stop positions when the at least one detector 107 (which may be a line detector) acquires intensity data as shown in FIG. 3. FIG. 3 illustrates a diagram of at least one embodiment of an intensity acquisition sequence that may be used in the step 50. The horizontal axis shows time, and the vertical axis shows wavelength, which is equivalent to position, in the bottom part of FIG. 3, and scan position in the top part of FIG. 3. The at least one detector 107 keeps acquiring intensity data. However, the at least one detector may stop acquiring intensity data when the motor 139 is in a transitional motion, such as when decelerating or accelerating. In the frame #1 as shown in FIG. 3, the at least one detector 107 acquires intensity data at the position #1 (P0) for an appropriate time for tissue characterization, such as 100 milliseconds ("msec"). At this moment, the motor 139 does not move and stays at the position P0, and the acquired intensity data is used for the tissue characterization and/or diagnosis. Then, after an appropriate or predetermined time, such as 100 msec, the motor 139 may start moving. The acquired intensity data when the motor 139 is moving is used for the SEE imaging. In the frame #2, until the motor 139 reaches the position #2 (P1), the acquired intensity data is used for the SEE imaging. When the motor 139 reaches the position P1, the motor 139 stops but the at least one detector 107 keeps acquiring intensity data that is used for the tissue characterization and/or diagnosis. When the at least one detector 107 acquires adequate intensity data for the tissue characterization and/or diagnosis, such as at or around 100 msec, the motor 139 starts moving. In frame #3 and frame #4, the stop position for the tissue characterization and/or diagnosis is different (e.g., P2 for frame #3 and P3 for frame #4), and intensity data is acquired for imaging at the other times (e.g., other than P2 and P3 for frame #3 and frame #4, respectively) of the respective frames. Changing stop positions achieves the step-scanning and obtains tissue information for a whole SEE image. Additionally or alternatively, frames #1 to #4 may be taken or processed in any other order to obtain intensity data. Scan position directions may be from top to bottom, bottom to top, left to right, right to left, or any other predetermined direction or directions to achieve or obtain the data.

Figure 5B:
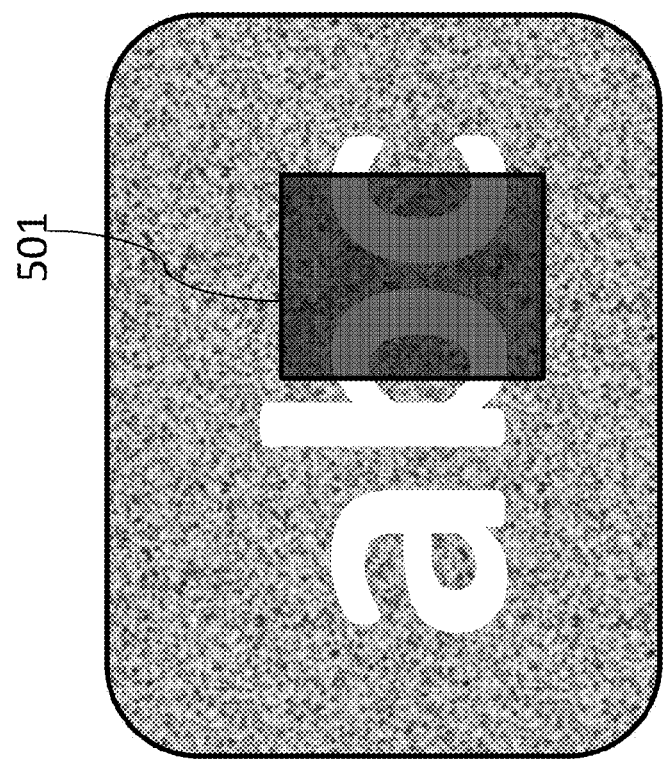
FIGS. 5A-5B are diagrams showing further embodiments of user interfaces for selecting a region of interest for measuring or characterizing tissue type using a SEE apparatus or system in accordance with one or more aspects of the present disclosure.

In the step 60, the computer, such as the console or computer 1200, 1200', determines if a line (e.g., line 401 as shown in FIG. 4) or region of interest (ROI) (e.g., ROI 501 shown in FIG. 5A, band ROI 502 shown in FIG. 5B, a predetermined ROI designated by a user, etc.) is designated as the specific region for displaying the tissue type. An operator or user selects a line or a region of interest (ROI) for the tissue characterization and/or diagnosis in the image, and the computer, such as the console or computer 1200, 1200', receives the operation input corresponding to the operator's selection. If it is determined that a line is designated, the method proceeds to the step 70. The computer, such as the console or computer 1200, 1200', causes a display (e.g., the display 1209) to display a graphical user interface for letting the operator decide a position of a line in the image, as shown in FIG. 4. If it is determined that an ROI is designated, then the method proceeds to the step 80. The computer, such as the console or computer 1200, 1200', causes a display (e.g., the display 1209) to display a graphical user interface for letting the operator decide a position of an ROI in the image, as shown in example GUIs in FIGS. 5A and 5B. In the GUIs shown in FIGS. 4-5B, an operator can choose and move a line (e.g., line 401 shown in FIG. 4, a predetermined line designated by a user, etc.) or ROI (e.g., ROI 501 shown in FIG. 5A, band ROI 502 shown in FIG. 5B, etc.) to the clinically interesting or predetermined positions to characterize and/or diagnose tissue. In the embodiment of FIG. 5B, a hand area ROI 502, which may be a type of an ROI that extends from the top of the image to the bottom of the image, is designated for measuring tissue type. In at least one embodiment, the band area 502 extends towards a direction perpendicular to the scanning direction of the illumination light (e.g., the illumination light 105) so, even if only a part of the band area 502 is designated, the tissue type information can be obtained in the entire band area 502 with very little additional time for processing. If a partial area in the band area 502 is designated, the scanning speed is slower in the band area 502 than in the other area in the image, so the image quality may be different between the inside and the outside of the band area 502. By superimposing an image indicating the tissue type information on the tissue image, the difference of the image quality in the image would not be noticed by an operator in one or more embodiments.

After the step 70 or the step 80, the method proceeds to step 90. In the step 90, the computer, such as the console or computer 1200, 1200', controls the MCU 140 to measure the tissue type in the designated area in the image. In one or more embodiments, the computer, such as the console or computer 1200, 1200' may include the MCU 140.

In one embodiment, whether the tissue type of the object is to be measured or types of a region in which the tissue type is to be measured is determined as imaging conditions designated in the step 04. Whether and how the tissue type is measured depends on the type or purpose of the characterization, diagnosis and/or examination, so multiple sets of imaging conditions may be stored in the hard disk 1204 (see FIG. 18) or SSD 1207 (see FIG. 19) and each of the imaging conditions is related to information of a characterization, diagnosis and/or examination purpose. Using an operation input for selecting the purpose of an examination, characterization and/or diagnosis, the computer, such as the console or computer 1200, 1200', designates one of the stored sets of imaging conditions, based on the relations between the stored sets of imaging conditions and the information of a purpose of an examination, characterization and/or diagnosis. Thus the whether and how the tissue type is measured is set, which reduces the operation tasks of the operator.

Figure 6:
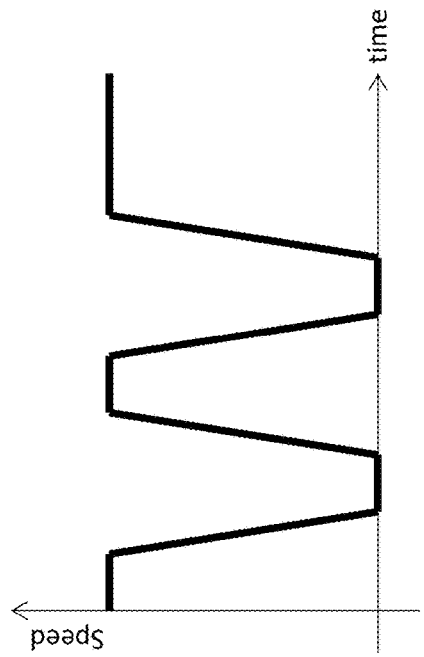
FIG. 6 is a graph illustrating an embodiment for a motor control method to acquire intensities for tissue characterization in accordance with one or more aspects of the present disclosure.

At least two motor controlling methods may be used in the step 10 to acquire intensities for the tissue characterizing mode. In the first controlling method in the step 10, a motion control unit (MCU), such as the MCU 140, changes and stops a motor, such as the motor 139, completely before the SEE probe reaches the diagnostic area as shown in FIG. 6. For example, the motor 139 is stopped as shown in FIG. 6 before the SEE probe reaches a diagnostic area, and then the motor 139 starts again to acquire intensity data.

In the step 90, the computer, such as the console or computer 1200, 1200', makes the display keep displaying a last image that was taken in the step 10 during the diagnostic mode. In some embodiments, this "last-image hold (LIH)" process is started in the step 20 or step 40, instead of in the step 10. The computer, such as the console or computer 1200, 1200', holds the last image which has been taken before the step 20 or the step 40 was completed. The display (e.g., the screen or display 1209 as shown in FIG. 18 or FIG. 19) keeps displaying the last image during the user operation, which makes the operator easier to designate the position of the line (e.g., the line 401 in FIG. 4) or the ROI (e.g., the ROI 501 in FIG. 5A, the band ROI 502 in FIG. 5B, etc.) in which the tissue type is to be measured, seeing the displayed still tissue image. When the motor motion is completely stopped, the at least one detector 107 starts acquiring intensity from the region in the image selected in the step 70 or step 80. Or, in one or more embodiments, the at least one detector 107 may keep acquiring intensities during the diagnostic mode, and unnecessary intensity data may be dumped after the acquiring. In at least one embodiment, while the still image is displayed in one or more of the steps 40, 60, 70 or 80), the computer, such as the console or computer 1200, 1200', continues to acquire tissue images. When the line (e.g., the line 401 in FIG. 4) or the ROI (e.g., the ROI 501 in FIG. 5A, the band ROI 502 in FIG. 5B, etc.) is designated in the step 70 or the step 80 the computer, such as the console or computer 1200, 1200', locates the designated line (e.g., the line 401 in FIG. 4) or the ROI (e.g., the ROI 501 in FIG. 5A, the band ROI 502 in FIG. 5B, etc.) on the current frame image by using one of the known pattern matching techniques.

Figure 7:
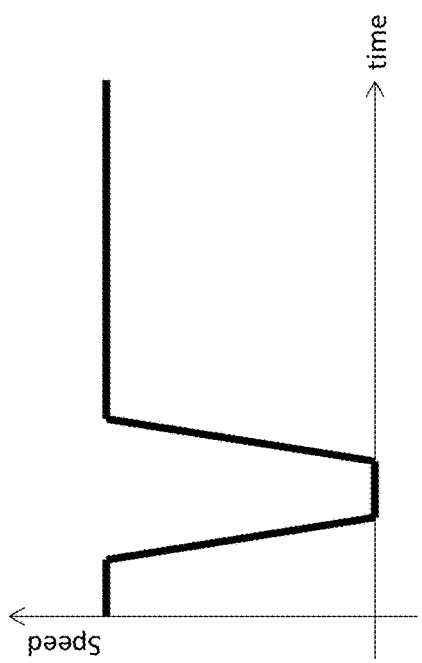
FIG. 7 is a graph illustrating another embodiment for a motor control method to acquire intensities for tissue characterization in accordance with one or more aspects of the present disclosure.

Additionally or alternatively, the intensity data acquired when the speed of the motor 139 is changing may be used to calculate tissue viscosity for a faster measurement. In a case where multiple lines or ROIs, or multiple groups of single lines or single ROIs, are selected by the operator in the step 70 or the step 80, the MCU 140 stops the motor 139, moves the motor 139 to the next selected position (e.g., for each selected line or ROI), and then starts and/or stops the motor 139 as shown in FIG. 7. In any cases, the data acquired by the at least one detector 107 is used for two purposes, i.e., displaying an image and storing intensity data for calculating a speckle intensity autocorrelation function as shown in step 100.

Figure 8:
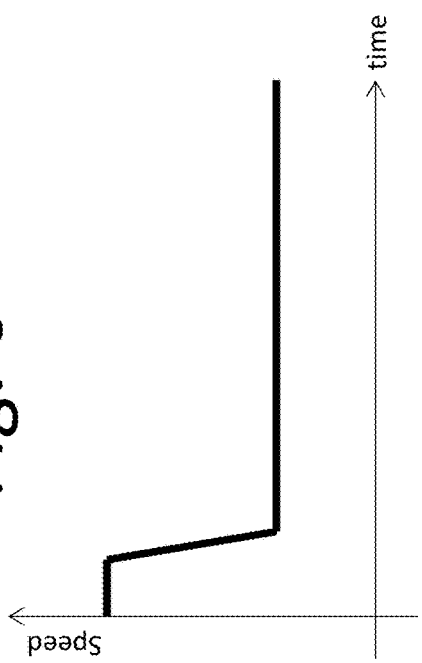
FIG. 8 is a graph illustrating yet a further embodiment for a motor control method to acquire intensities for tissue characterization in accordance with one or more aspects of the present disclosure.

As shown in FIG. 8, the MCU 140 may decrease the speed of the motor 139, and not stop the motor 139 completely, for the diagnostic mode. In this case, the time required to diagnose the tissue type can be improved. For example, time is saved by not stopping the motor 139 completely. By way of at least one example and while other embodiments may use different speeds or ranges of speeds, the speed of the motor 139 may be reduced to a particular range of speeds, in at least one embodiment. For example, in at least one embodiment, a required data length for calculating an intensity autocorrelation function may be $T_{AF}=100$ msec, and a horizontal length of a ROI may be $L_x=1$ mm. When one value of viscosity within the ROI may be needed, the velocity may be calculate using the following equation:

$$\text{Velocity} = \frac{L_x}{T_{AF}} = 10 \text{ mm/sec}$$

Then, the reduced speed range can be described as the following:

$$\text{Velocity} = 0 \sim \frac{L_x}{T_{AF}}$$

Or, when the $T_{AF}=100$ msec is fixed, Velocity=$0\sim10\cdot L_x$ m/sec.

In the step 100, the stored successive line data in time domain can be analyzed as the time-varying speckle intensity data to obtain intensity autocorrelation function $g2(\tau, \lambda)$ using the below equation. The process may also performed by the computer, such as the console or computer 1200, 1200'. In one or more embodiments, the function $g2(\tau, \lambda)$ is calculated using the following equation:

$$g_2(\tau, \lambda) = \frac{\langle I(t, \lambda) \cdot I(t+\tau, \lambda) \rangle}{\langle I(t, \lambda) \rangle^2}.$$

In this equation, the I is intensity, the t is time, the $\lambda$ is wavelength and corresponds to the vertical axis in the SEE system, the $\tau$ is time lag between 2 intensity data, and angle bracket < > means average over time, t. When the input laser intensity is fluctuated in time, the following equation may be used:

$$g_2(\tau, \lambda) = \frac{\langle I(t, \lambda) \cdot I(t+\tau, \lambda) \rangle}{\langle I(t, \lambda) \rangle \langle I(t+\tau, \lambda) \rangle}.$$

The intensity autocorrelation function g2(τ, λ) may be calculated in each vertical position along a line or ROI.

Figure 9A:
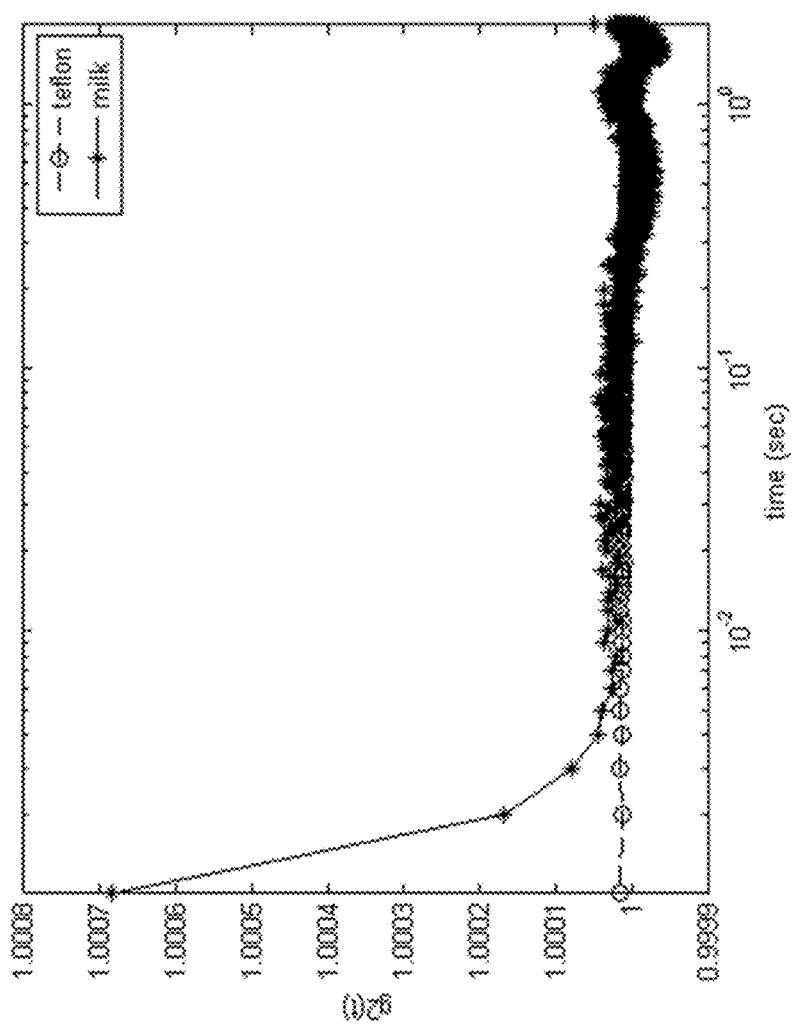
FIG. 9A is a graph illustrating speckle intensity autocorrelation functions of Teflon and milk at 1000 lines per second in accordance with one or more aspects of the present disclosure.

FIG. 9A shows representative speckle intensity autocorrelation function g2(τ) curves that are averaged over the wavelength using a rigid Teflon block and milk. The horizontal axis shows logarithmic time and the vertical axis shows a speckle intensity autocorrelation. The at least one detector 107 (also referred to as the line detector) frame rate is 1000 lines per second, the pixel size is 1×2048 pixels, and the measurement time is 2 seconds. The g2(τ) may also be represented using a field autocorrelation function g1(τ) and β being related to experimental parameters as shown in the following equation:

$$g_2(\tau) = 1 + \beta(g_1(\tau))^2,$$

where β is a coherence factor, and an autocorrelation of electric fields is described as the following when a detected light meets the collision broadened condition:

$$g_1(\tau) = e^{-i\omega_0\tau - \left(\frac{|\tau|}{\tau_c}\right)},$$

where $\omega_0$ is a frequency of the light, τ is a time lag, and $\tau_c$ is a decay time. Then the whole obtained autocorrelation functions may be fitted using the following exponential equation:

$$g_2(\tau) = 1 + \beta \cdot e^{-\frac{\tau}{\tau_c}},$$

where β is a coherence factor, $\tau_c$ is a decay time, also known as a time constant. For example, in one or more embodiments, β may be 0.0007.

Since the teflon block has high viscosity, the speckle intensity and pattern rarely change, and the g2(τ) curve is flat around 1 or 2 seconds. On the other hand, since the milk has low viscosity, the speckle intensity and pattern change rapidly, and the g2(τ) curve decays quickly starting with a certain β value. The decay time may be calculated by a fitting exponential function. Based on the decay time and the β value of the g2(τ) curves, relative viscosity may be quantitatively identified by the post-processing in the SEE console or computer, such as the console or computer 1200, 1200'. For example, in one or more embodiments, the viscosities of sample material or tissue (e.g., object 130) are measured by standard equipment, such as a rheometer, in advance and a look-up table may be prepared in the SEE console, such as the console or computer 1200, 1200', in advance. Using the up-front stored look-up table, the measured decay time and β value allows the SEE console, such as the console or computer 1200, 1200', to characterize tissue types, other biological sample or samples (e.g., blood, body fluid, mucus, etc.) and/or other characteristic(s) of the biological objects, in the image. Different sample types, such as a tissue, mucus, blood, etc., may have similar viscosity, or the same sample type may have different viscosities, under different conditions.

Figure 20:
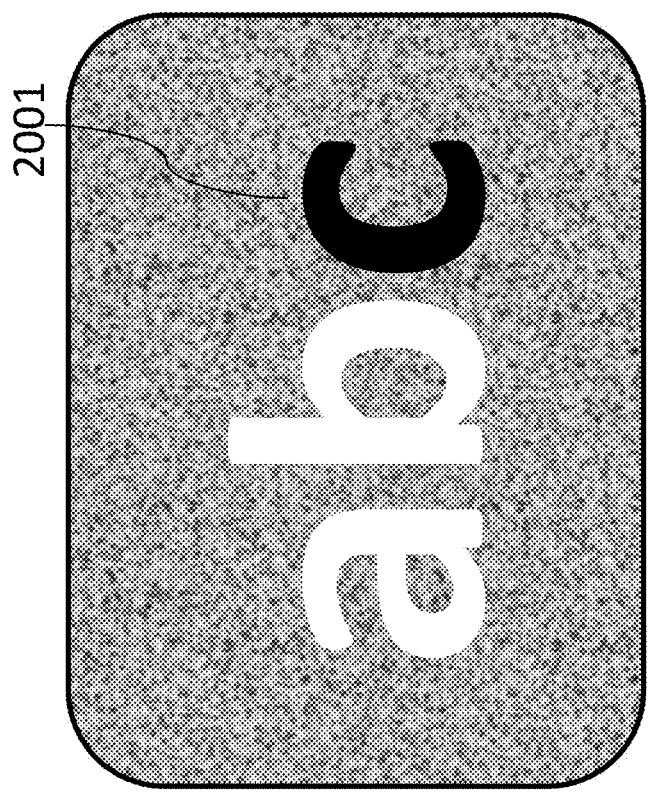
FIG. 20 is a diagram showing an embodiment of a user interface displaying areas having at least one different color from each other to distinguish sample type in accordance with one or more aspects of the present disclosure.

In the step 110, the computer, such as the console or computer 1200, 1200', causes a display (e.g., the display or screen 1209 as shown in FIG. 18 or FIG. 19) to display the tissue type information together with the reconstructed tissue image. The tissue type is distinguished in a different color in overlapped fashion on the scanned morphological image on the display (e.g., the display or screen 1209 as shown in FIG. 18 or FIG. 19) as illustrated in FIG. 20. The area 2001 in FIG. 20 has different color to distinguish sample (e.g., tissue) type. In one embodiment, the computer, such as the console or computer 1200, 1200', switches displayed images between a tissue image in which the tissue type information is superimposed on the tissue image, and a tissue image in which a frame of the selected region for measuring the tissue type is displayed. The computer, such as the console or computer 1200, 1200', switches the displayed images in response to the operation input from the operation unit (e.g., such as, but not limited to, a mouse device 1211, a keyboard 1210, a touch panel device, etc.), which makes the operator compare the original tissue image and the tissue image in which the tissue type information is superimposed. As the object to be imaged or the probe moves, the computer, such as the console or computer 1200, 1200', may continuously track the location of the selected line (e.g., the line 401 of FIG. 4) or ROI (e.g., the ROI 501 of FIG. 5A, the band ROI 502 of FIG. 5B, etc.) on the current frame image.

In the step 120, the computer, such as the console or computer 1200, 1200', determines if the examination, characterization and/or diagnosis is ended, according to an operation input from the operation unit (e.g., such as, but not limited to, a mouse device 1211, a keyboard 1210, a touch panel device, etc.). While an operation input for ending the examination, characterization and/or diagnosis is received, the computer, such as the console or computer 1200, 1200', keeps displaying the tissue image in which the tissue type information is superimposed. In one embodiment, the computer, such as the console or computer 1200, 1200', provides a graphical user interface to change or add the region in which the tissue type is to be measured (see e.g., FIGS. 4-5B). In at least one embodiment, if the operation input for changing the region is received during the loop of the steps 110 and 120, the computer, such as the console or computer 1200, 1200', the process proceeds to the step 20.

Once the tissue type is measured in the selected region, the SEE system (e.g., the system 100, the system 1100, etc.) continuously acquires the tissue images without measuring the tissue type, while the measured tissue type information is superimposed on the tissue images acquired after the tissue type is measured.

Due to the movement of the probe (or one or more components thereof) or the object to be imaged, the selected region or the LIH images may be outside the current image. In one embodiment the computer, such as the console or computer 1200, 1200', causes the display (e.g., the display or screen 1209) to display both the LIH image for designating the line (e.g., the line 401 of FIG. 4) or the ROI (e.g., the ROI 501 of FIG. 5A, the band ROI 502 of FIG. 5B, etc.), and the current tissue images. In one or more embodiments, it may be helpful to display on the current tissue image a frame indicating the imaging region of the image. The imaging region may be determined by the computer, such as the console or computer 1200, 1200', applying the known pattern matching technique to the LIH image and the tissue images acquired after the LIH image is acquired.

In one or more embodiments, a commercially available motor (e.g., such as the motor 139) may be deaccelerated and accelerated within 0.2 msec, and a commercial available line camera or detector (which may be used as the at least one detector 107) has 2048 pixels with 140 kHz. Then the SEE image may be captured in 2000 pixels in a wavelength direction and 500 pixels in a scanning direction with 10 fps (frames per second). Based on the g2(τ) curves in FIG. 9A, the time to calculate the decay time and the β value is 10 msec. Alternatively, in one or more embodiments, camera specifications may be one of the following: 4096 pixels with 140 kHz, 2048 pixels with 100 kHz, 2048 pixels with 200 kHz, or 4096 pixels with 200 kHz.

In the case of the step 60 with the FIG. 4 situation, since the motor 139 stopping period can be 10 msec, the required time for characterizing tissue type in measurements is 10.4 msec per a line in the subject scenario. In the case of the step 60 with the FIG. 5A situation, for example the 100×100 pixels of the ROI is selected for characterizing tissue type, the required time for measurement is 1.04 sec. to measure the entire ROI in the subject scenario.

Figure 5A:
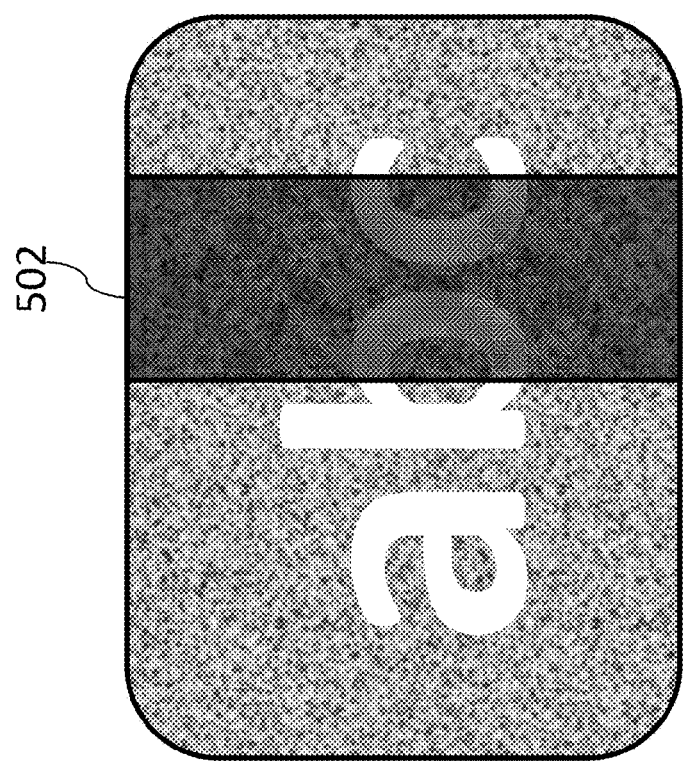

For the step 70, the scanning speed may be 1 fps (1/10 of the initial speed), which is equivalent to 2 msec per a line. Since obtaining 10 msec data needs 5 lines, then spatial resolution becomes 1/5. For example, the 100×100 pixels of the ROI (e.g., the ROI 501 of FIG. 5A) is selected for characterizing tissue type as shown in FIG. 5A, the required time for measurement is about 0.2 sec. in the subject scenario. In this case, the tissue characterization may be performed quickly compared to the last case instead of losing spatial resolution.

For the step 80, since the measurement time of 10.4 msec for characterizing tissue type is applied to whole 500 lines, then the required time for characterizing tissue type in a scanned image is 5.2 sec. (0.0104×500) in the subject scenario. When the sweeps stopping positions skip every other line, the required time for characterizing tissue type becomes 2.6 sec. in the subject scenario.

Since the post-processing for calculating the decay time and the β value from the $g2(\tau)$ curves may be performed during the measurement, then it rarely affects a time to obtain the tissue type identification.

Figure 9B:
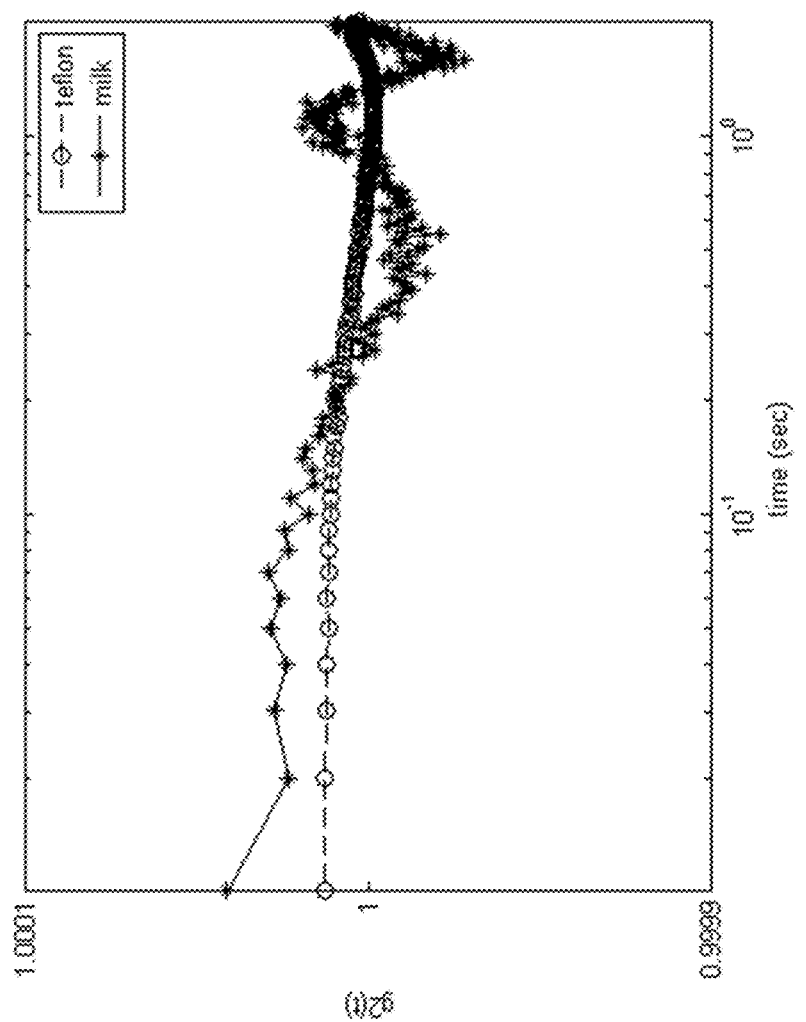
FIG. 9B is a graph illustrating speckle intensity autocorrelation functions of Teflon and milk at 100 lines per second in accordance with one or more aspects of the present disclosure.

Even though the $g2(\tau)$ curves with 1000 lines per sec. in FIG. 9A may obviously distinguish tissue type, using 140 kHz (line per sec) data acquisition may improve the stability of calculating the decay time and the β value of $g2(\tau)$ curves. FIG. 9B illustrates another representative speckle intensity autocorrelation function $g2(\tau)$ curves that is averaged over the wavelength using a rigid teflon block and a milk with lower 100 line per sec. In this case, the tissue type can be distinguished and the required time for calculating the decay time and the β value of $g2(\tau)$ curves can be suppressed such that calculating time may be saved. For example, because data amount of 100 lines per second is 1/10 of 100 lines per second, the calculating time takes less time when using a data amount of 100 lines per second rather than 1000 lines per second.

Since the $g2(\tau, \lambda)$ depends on the wavelength ($\lambda$) and since the penetration depth in tissue also depends on the wavelength, viscosity measurement may be performed with different depth. For example, in one or more embodiments, the wavelength (or range of wavelengths) may be selected based on the biological or optical parameters of a particular application, for example, the wavelength may be determined by hemoglobin and oxidized hemoglobin on the blue wavelength side (see e.g., right side of FIG. 11B) and by water absorption on the near infrared side (see e.g., left side of FIG. 11B). In one or more embodiments, one particular useful range is the optical window range from about 600 nm to about 1300 nm (see e.g., FIG. 11B).

Figure 10:
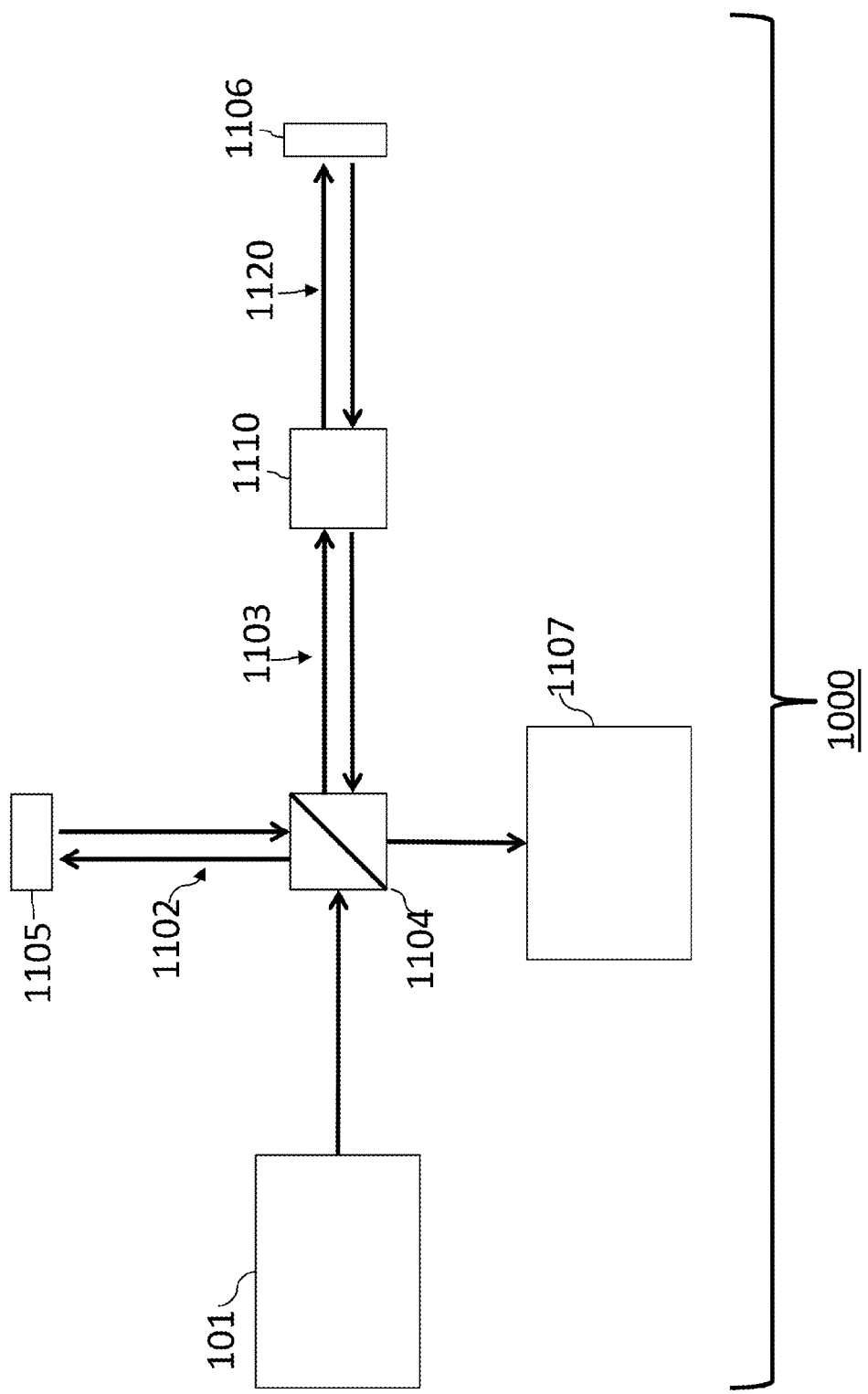
FIG. 10 is a diagram showing an embodiment of an OCT system at may be used with one or more features of the present disclosure.

This tissue type characterization using speckle intensity autocorrelation function may be applied to an optical coherent tomography (OCT) system with an optical rotary junction in one or more embodiments. Changing the speed of the optical rotary junction may obtain adequate speckle data for processing the $g2(\tau)$ and for determining the tissue type. Then, the overlapped images of the OCT and the tissue type distinguished in different colors may be displayed. This embodiment may be used for industrial purposes, such as a videoscope or a fiberscope for detecting material types through a small hole or cavity. FIG. 10 shows an exemplary system 1000 which can utilize the OCT technique. A light from a light source 101 delivers and splits into a reference arm 1102 and a sample arm 1103 with the splitter 1104. A reference beam is reflected from a reference mirror 1105 in the reference arm 1102 while a sample beam is reflected or scattered from a sample 1106 through a PIU (patient interface unit) 1110 and a catheter 1120 in the sample arm 1103. The PIU 110 may include a rotary junction for rotation of the catheter 1120. Both beams combine at the splitter 1104 and generate interference patterns. The output of the interferometer is detected with detector(s) 1107, such as, but not limited to, photodiode(s) or multi-array camera(s). The interference patterns are generated only when the path length of the sample arm 1103 matches that of the reference arm 1102 to within the coherence length of the light source 101.

FIG. 11A shows an alternative embodiment of a forward-viewing Spectrally Encoded Endoscopy ("SEE") system 1100 (also referred to herein as "system 1100" or "the system 1100") which operates to utilize a SEE technique with speckle detection for optical probe applications in accordance with one or more aspects of the present disclosure. The system 1100 is similar to the system 100 described above except that the system 1100 further includes a prism 109 at the end of the SEE probe and before the DG 104 to illuminate the light perpendicular to a probe axis (e.g., an optical axis of the SEE probe, an optical axis of the SEE system, an axis that extends substantially parallel to or along the IF 102 and/or the DF 103, an axis that extends perpendicular with respect to the prism 109 and/or the diffraction grating 104, etc.). In other words, the only difference between the embodiment of FIG. 1 and the embodiment of FIG. 11A is viewing direction where the embodiment of FIG. 11A includes the prism 109 to change light direction. The structure of the DG 104 may be the same for the system 100 and the system 1100 in one or more embodiments. In one or more embodiments, a prism, such as the prism 109, may combine a gradient-index (GRIN) lens and an optional angled spacer. In one or more embodiments, a prism may operate as, or be substituted with, a spacer element. In one or more embodiments, an optic axis may be at least one of: an axis along which there is, or is some degree of, rotational symmetry in an optical system; an axis that defines a path along which light from the light source 101 spreads through an optical system (such as, but not limited to, the system 100, the system two, the system 1600, the system 1700, etc.); an axis that defines a path along which there is, or is some degree of, rotational symmetry in an optical system (such as, but not limited to, the system 100, the system 1100, the system 1600, the system 1700, etc.); an axis along a core of an optical fiber (see e.g., the fiber 102, the fiber 103, etc.); an optical axis along a center of a core of an optical fiber (see e.g., the fiber 102, the fiber 103, etc.); an axis defining a path passing through a collimation field and along which there is, or is some degree of, rotational symmetry; etc.

Figure 12:
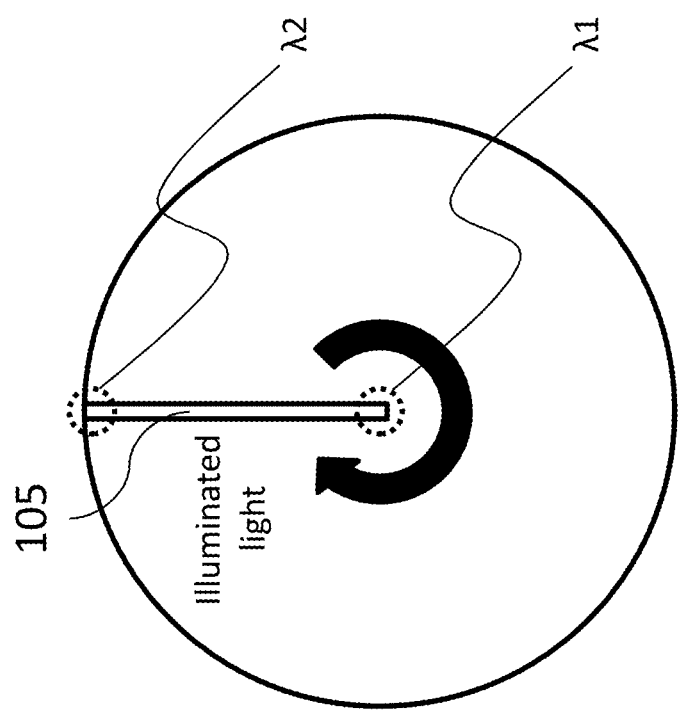
FIG. 12 is a diagram showing an embodiment of an illuminated area with rotation around a position of λ1 in accordance with one or more aspects of the present disclosure.
Figure 15:
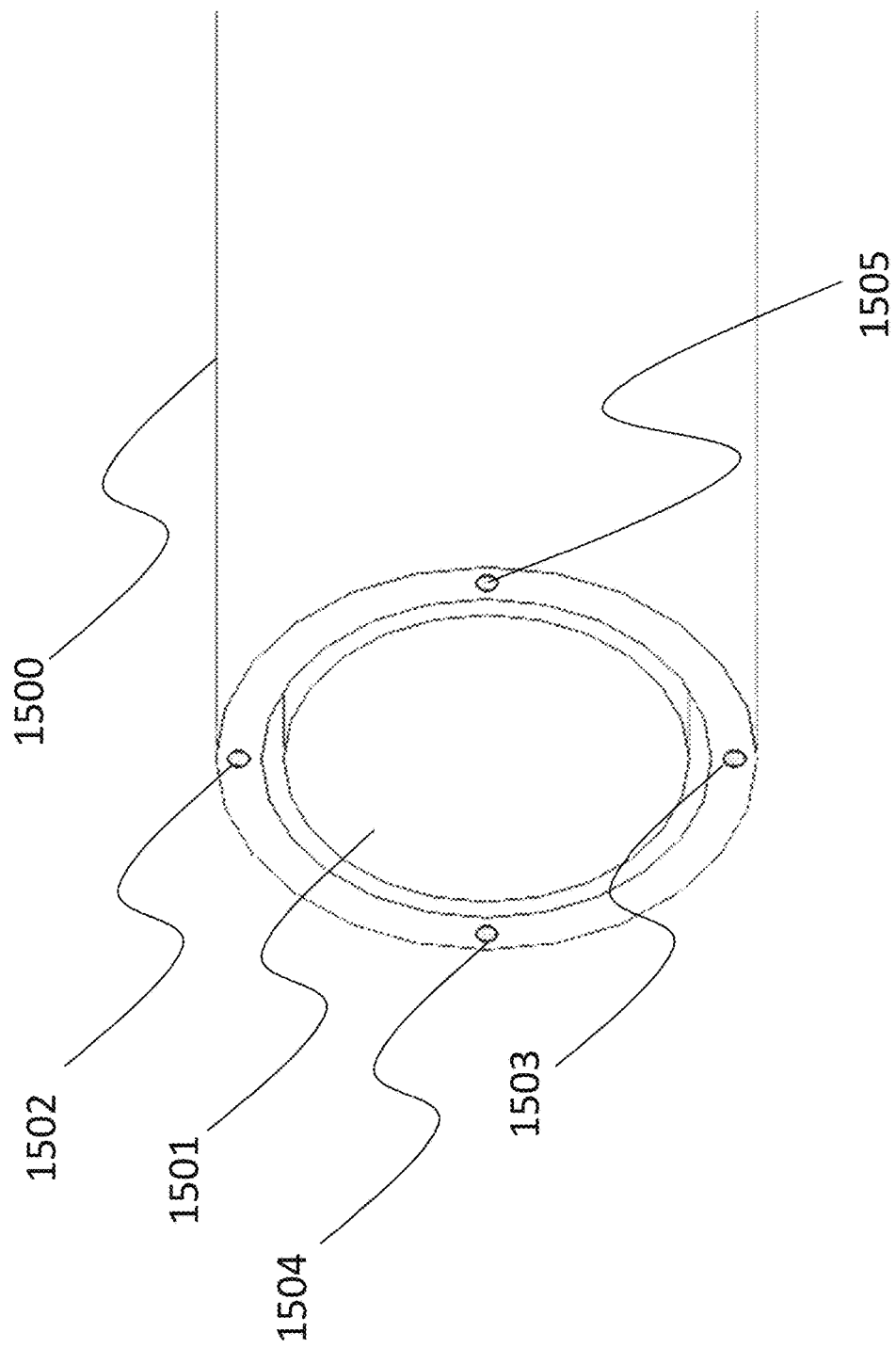
FIG. 15 is a diagram illustrating at least one embodiment of a SEE probe with a tendon system in accordance with one or more aspects of the present disclosure.

As such, descriptions of like-numbered elements present in the system 1100 and already described above shall not be repeated, and are incorporated by reference herein in their entireties. As shown in FIG. 12, the illuminated light 105 at the tissue or object rotates 360 degrees to obtain the forward-viewing SEE image. In this case, the position λ1 stays at the center of the scanning image, and the position λ2 rotates on the edge of the scanning image. The SEE system 1100 in this embodiment also includes a tendon-driven probe changing the view of the SEE probe 1501 as illustrated in FIG. 15 (further discussed below). The probe 1501 may include multiple tendons (e.g., the tendons 1502, 1503, 1504, 1505 as shown in FIG. 15) connected to a tendon control unit (which may be included in the console or computer, such as the computer 1200, 1200') including actuators to push and pull the tendons 1502, 1503, 1504, 1505 to change the direction of the distal end of the probe 1501. In one or more embodiments, the tendon control unit may be connected with the computer, such as the computer 1200, 1200', via the operation interface (e.g., operation I/F 1214 as shown in FIG. 19; communication interface 1205 as shown in FIG. 18; etc.) or the network interface (e.g., network I/F 1212 as shown in FIG. 19; the communication interface 1205 and/or the network 1206 as shown in FIG. 18; etc.), and computer, such as the computer 1200, 1200', sends and receives the control signals and status information to control the probe 1501.

Figure 13:
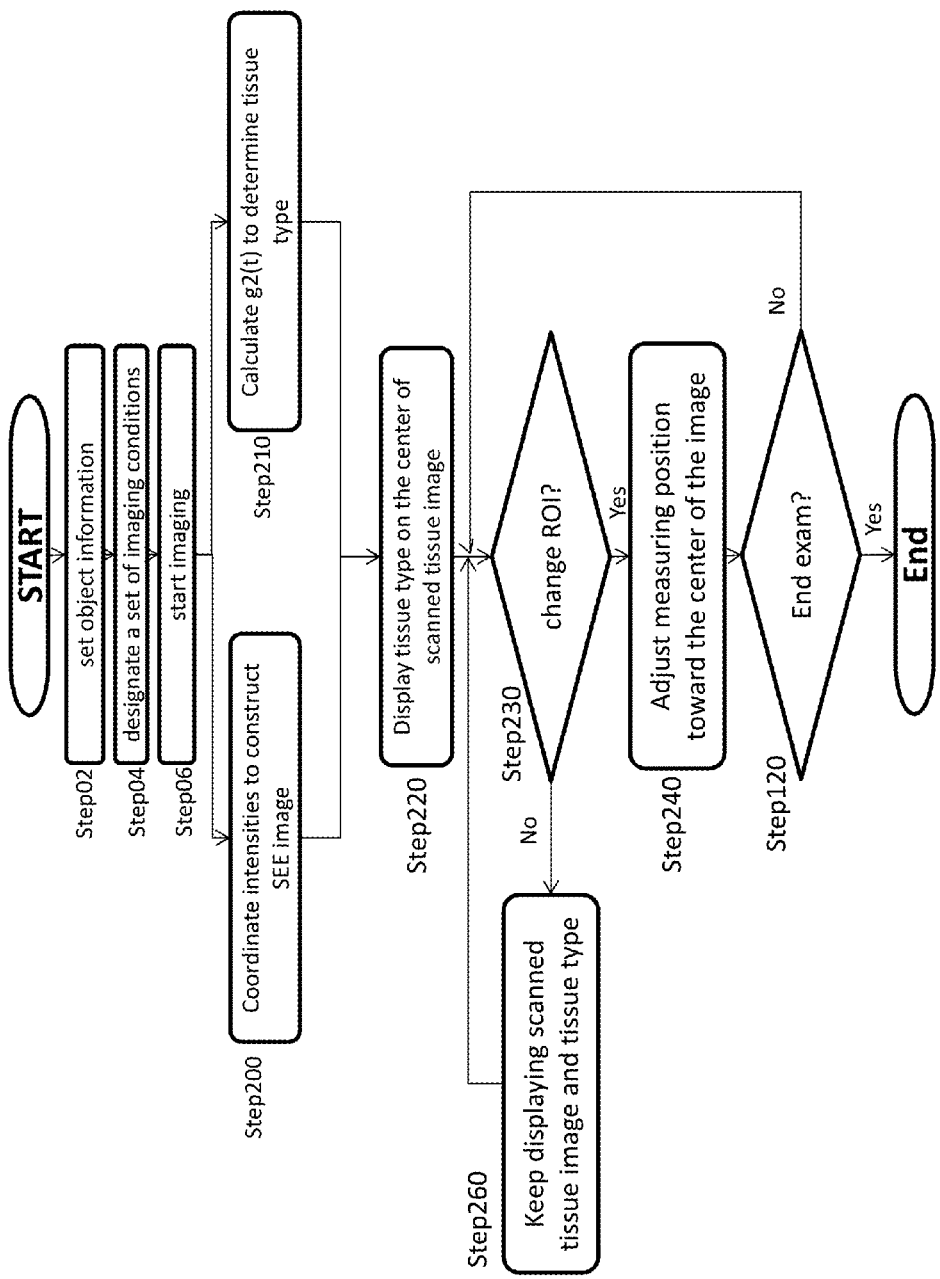
FIG. 13 is a flowchart illustrating at least one embodiment of a method for using or use with a forward-viewing SEE system with speckle detection for characterizing tissue in accordance with one or more aspects of the present disclosure.

In accordance with at least one aspect of the present disclosure and as aforementioned, one or more methods for performing tissue characterization when using a forward-viewing SEE system (such as the system 1100) with speckle detection are provided herein. FIG. 13 illustrates a flow chart of at least one embodiment of a method for characterizing tissue using a forward-viewing SEE system (e.g., with the SEE system of FIG. 11A). Preferably, the method(s) may include one or more of the following: (i) setting object information (see step 02 in FIG. 13); (ii) designating one or more imaging conditions (see step 04 in FIG. 13); (iii) start imaging (see step 06 in FIG. 13); (iv) coordinating intensities to construct a SEE image (see step 200 in FIG. 13); (v) calculating g2(t) to determine tissue type (see step 210 in FIG. 13); (vi) displaying tissue type on a center (or other predetermined location) of a scanned tissue image (see step 220 of FIG. 13); and (vii) determining whether to change the ROI (see step 230 in FIG. 13; (viii) if "Yes" in step 230, then adjust a measuring position toward the center of the image (see step 240 in FIG. 13) and then determine whether to end the exam (see step 120 of FIG. 13; if "No", repeat step 230, and if "Yes", end the process), or if "No" in step 230, then keep displaying the scanned tissue image and tissue type (see step 260 of FIG. 13) and then repeat step 230. The descriptions of the same or similar steps from the flowchart of FIG. 2 (which already have been described above) that are included in the flowchart of FIG. 13 are omitted here.

In the step 200, the computer, such as the computer 1200, 1200', in the SEE system 1100 coordinates position dependent intensities to construct the 2D image of the tissue or object 1500. At the same time, the speckle intensity autocorrelation function $g2(\tau)$ at the position of the $\lambda 1$ is calculated in the step 210. In one or more embodiments, steps 200 and 210 may be performed at different times. Similarly to the system 100 described above and in one or more embodiments of the system 1100, the viscosities of sample material or tissue (e.g., the object 130) may be measured by standard equipment, such as a rheometer, in advance, and a look-up table may be prepared and stored in the SEE console, such as the computer 1200, 1200', in advance. Using the up-front stored look-up table, the measured decay time and the β value makes the computer, such as the computer 1200, 1200', characterize tissue types at a predetermined location, such as the center, of the SEE image. In the step 220, the tissue type (which may be distinguished in different color in one or more embodiments) is overlapped on a predetermined location (such as the center) of the scanned morphological image on the display (e.g., the screen or display 1209 as shown in FIG. 18 or FIG. 19), by the computer, such as the computer 1200, 1200'. In at least one embodiment of the step 230, the computer, such as the computer 1200, 1200', may cause the display (e.g., the display or screen 1209 as shown in FIG. 18 or FIG. 19) to display a graphical user interface to let an operator change a region, or may determine whether to change the ROI, to select a clinically interesting or predetermined tissue position. If an operator does not select any positions or if the system 1100 determines that no change of a line or ROI is needed, the process proceeds to the step 260 directly. If an operator selects a line or ROI in the image on the screen as shown in FIG. 14, the process proceeds to the step 240.

Figure 14:
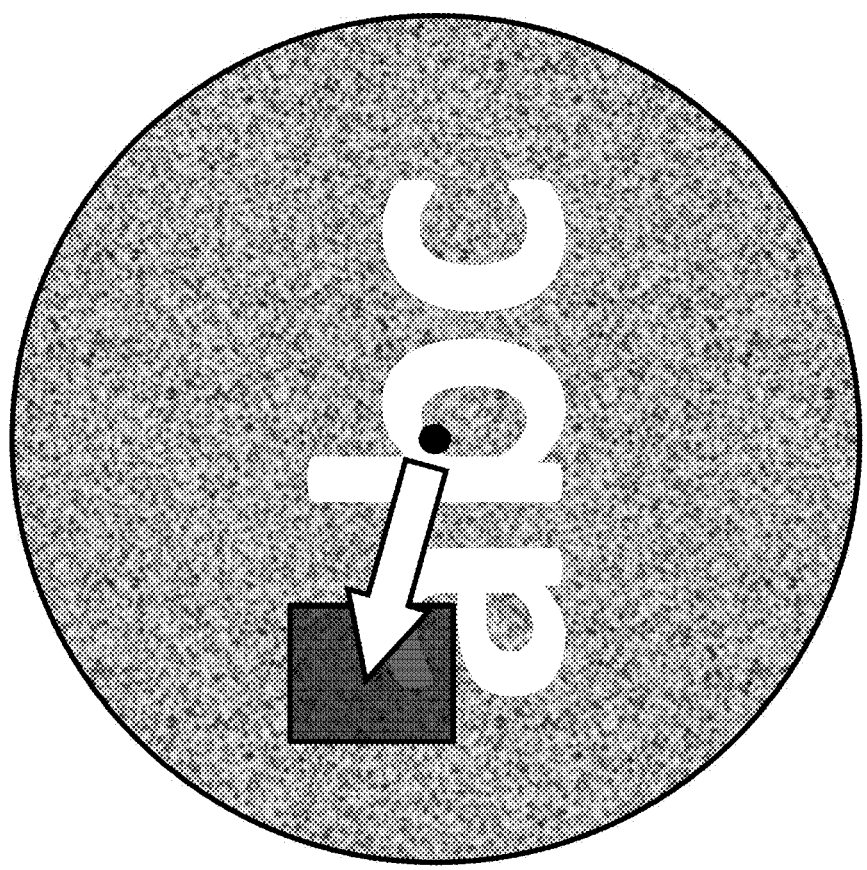
FIG. 14 is a diagram showing an embodiment of a user interface for selecting a region of interest for measuring or characterizing tissue type using a SEE apparatus or system in accordance with one or more aspects of the present disclosure.

In the GUI embodiment shown in FIG. 14, a center spot shows tissue type at the center of the image, and the half transparent square or rectangle shows an ROI that an operator selected. Additionally or alternatively, an ROI or a different ROI may have any geometric shape as desired by a user, including, but not limited to, rectangular, square-shaped, circular, ovular, triangular, etc. In at least one embodiment having multiple ROIs, one ROI may be differently sized and shaped as compared with another ROI. In the step 240, the computer, such as the computer 1200, 1200', transmits a control signal to the SEE probe controller to automatically adjust the probe position so that the center of the ROI matches the center of the image as the white arrow shows in FIG. 14.

As aforementioned, FIG. 15 shows a schematic of an embodiment of a SEE probe 1501 with tendons 1502, 1503, 1504, 1505. Based on the relationship between the center of the ROI and the center of the image (e.g., as shown in FIG. 14), the computer, such as the computer 1200, 1200', may control the tendon 1502 and 1503 for up-down (or down-up) motion and the tendon 1504 and 1505 for right-left (or left-right) motion. Those tendons 1502, 1503, 1504, 1505 are inside of the sheath 1500, and the sheath material may be bent due to stress applied by tendons 1502, 1503, 1504, 1505. In this embodiment, the SEE probe 1501 itself is rotating to obtain the image inside the sheath 1500. The sheath 1500 may be transparent or semitransparent, may be extruded, and may be single or multilayer. Because the displayed tissue images may be rotated, the upward, downward, rightward, and leftward directions of the display in which the tissue image is displayed and those directions of the image itself may not always coincide in one or more embodiments. As such, the computer, such as the computer 1200, 1200', may use information of the rotation angle of the displayed image to generate the control signals for determining how each of the tendons 1502, 1503, 1504, 1505 should be pushed or pulled. Various combinations of the tendons 1502, 1503, 1504, 1505 may be used to move the probe diagonally in one or more predetermined directions. As aforementioned, in the step 260 of FIG. 13, the computer, such as the computer 1200, 1200', causes the display (e.g., the display 1209 as shown in FIG. 18 or FIG. 19) to keep displaying the scanned tissue image and the tissue type. Alternatively, a sheath 1500 may include any predetermined number of tendons (e.g., one tendon, two tendons, three tendons, four tendons, etc.) depending on the desired mobility of the sheath 1500.

Figure 16:
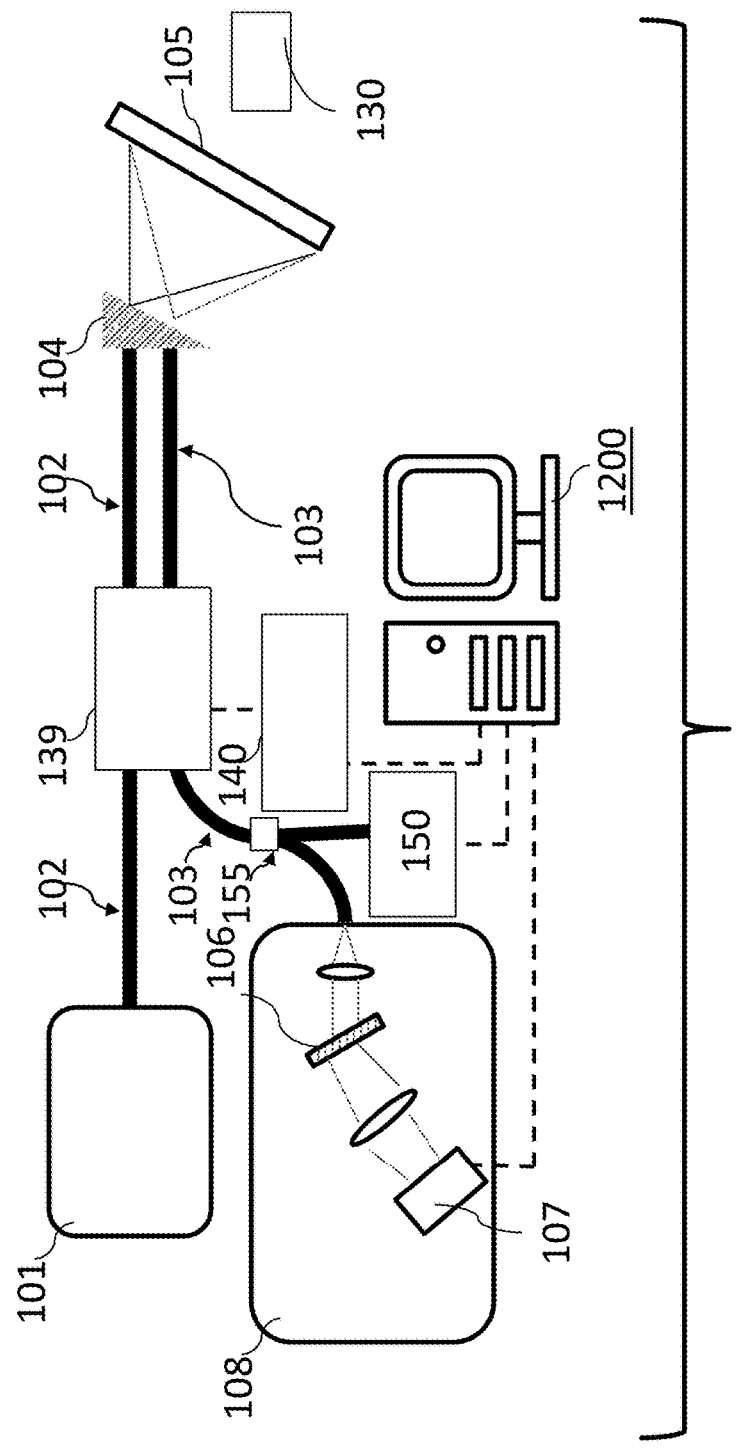
FIG. 16 is a diagram showing an embodiment of a SEE system with speckle detection using a photodiode in accordance with one or more aspects of the present disclosure.

FIG. 16 shows another alternative embodiment of a Spectrally Encoded Endoscopy ("SEE") system 1600 (also referred to herein as "system 1600" or "the system 1600") using a photodiode 150 which operates to utilize a SEE technique with speckle detection for optical probe applications in accordance with one or more aspects of the present disclosure. The system 1600 is similar to the system 100 described above except that the system 1600 further includes a photodiode 150 connected to the DF 103 and to the console, such as the console 1200, 1200'. Descriptions of like-numbered elements present in the system 1600 and already described above shall not be repeated, and are incorporated by reference herein in their entireties. As shown in the embodiment of FIG. 16, the photodiode 150 is at the proximal side of the system 1600 to detect time varying speckle intensities separated from a spectrometer (such as the spectrometer 108). In this case, the whole range of wavelength or windowed range of wavelength is averaged when the photodiode 150 obtains intensity data. For example, over 1 MHz lines per second can be achieved with reducing data size needed to be calculated for a speckle autocorrelation function $g2(t)$. While not limited to this arrangement, the photodiode 150 may be connected to a detection fiber (DF) 103 through a fiber coupler 155 (see FIG. 16). In one or more embodiments, the stored intensity data obtained by the photodiode may be solely used for calculating the speckle intensity autocorrelation function, so that the console, such as the console or computer 1200, 1200', can separate the SEE imaging and tissue characterization to stabilize the system 1600 (for example, in one or more embodiments, the at least one detector 107 may be used only for imaging and the photodiode 150 may be used only for calculating a speckle intensity autocorrelation function). The speckle intensity autocorrelation functions acquired in each scanning line may be more distinguishable for tissue characterization, because achievable Hz by a photodiode (such as the photodiode 150) may be much higher than when using at least one detector 107 (such as a line detector).

Figure 17:
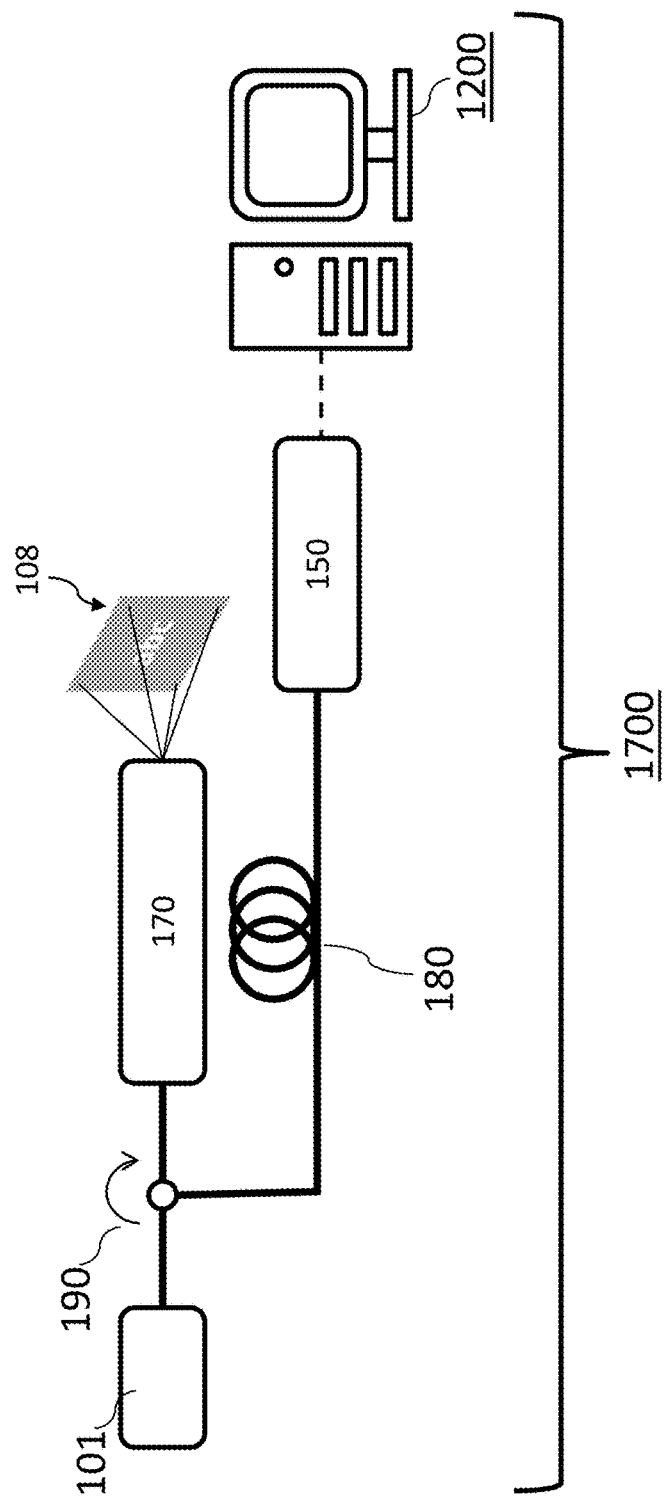
FIG. 17 is a diagram showing an embodiment of a serial time-encoded 2D imaging system with speckle detection in accordance with one or more aspects of the present disclosure.

In accordance with one or more further embodiments of the present disclosure, a serial time-encoded 2D imaging system with speckle detection is disclosed herein (best seen in FIG. 17). Descriptions of like-numbered elements present in the system 1700 (e.g., the light source 101; computer 1200, 1200'; etc.) and already described above shall not be repeated, and are incorporated by reference herein in their entireties. Tissue may be characterized using the serial time-encoded 2D imaging system 1700. A light, such as a broadband pulse laser, may be produced by the light source 101, and passes through a deflecting section, such as a circulator 190, and enters a 2D disperser 170, which includes two orthogonally oriented gratings. The 2D disperser 170 divides the incident light into 2D illumination lights with different wavelength at each 2D position (see element 108 shown in FIG. 17). The reflected lights are combined by the 2D disperser 170 and enter the deflecting section, such as the circulator 190, again. Next, the reflected lights pass through a dispersion compensating fiber 180, which makes chromatic dispersion and the intensity data reflected by a sample (see element 108 shown in FIG. 17) dispersed in a time domain. Then, intensities of each wavelength associating with the position at the sample (see element 108 shown in FIG. 17) may be distinguishable based on time delay detected at a photodiode 150. A console, such as a computer 1200, 1200', is preferably connected to the photodiode 150, stores intensity data and reconstructs images (and/or stores reconstructed images) of the sample (see element 108 shown in FIG. 17). By way of at least one example, Goda et al. achieved a frame rate of 6.1 MHz, the pixel size was 6.4 um×0.3 urn, and the field of view was 170 um×27 um. (see Goda, K., Tsia, K. K., & Jalali, B. Serial time-encoded amplified imaging for real-time observation of fast dynamic phenomena. Nature, 458(7242), 1145-1149 (2009)).

In some embodiments, the deflecting section, such as the circulator 190, operates to deflect the light from the light source 101 to the SEE probe, and then send light received from the SEE probe towards the at least one detector 107. In one or more embodiments, the deflecting section of the system 1700 may include or may comprise one or more interferometers or optical interference systems that operate as described herein, including, but not limited to, the circulator 190, a beam splitter, an isolator, a coupler (e.g., fusion fiber coupler), a partially severed mirror with holes therein, a partially severed mirror with a tap, etc.

Additionally or alternatively, the tissue characterizing serial time-encoded 2D imaging system 1700 has a function, which calculates viscosity of a sample (e.g., such as the object 130) using accumulated speckle fluctuations as described for at least systems 100 and 1100 or any other system described herein. As same as, or similarly to, the previous embodiments, $g2(t)$ curves are calculated based on intensities captured by a photodiode (such as the photodiode 150). In this case, since the 2D image is captured without any mechanical motions and the frame rate is adequate enough to calculate $g2(t)$ curves compared with system 100 and system two, the whole area of the overlapped morphological and viscosity image can be displayed with 10 fps. When, the frame rate is 10 fps, the tissue type map may be refreshed by every 100 msec, which can distinguish milk and Teflon as shown in FIG. 9A and/or FIG. 9B.

In one or more embodiments, a SEE probe may be connected to one or more systems (e.g., the system 100, the system 1100, the system 1600, the system 1700, etc.) with a connection member or interface module. For example, when the connection member or interface module is a rotary junction for either a SEE probe or the aforementioned OCT system, the rotary junction may be at least one of: a contact rotary junction, a lenseless rotary junction, a lens-based rotary junction, or other rotary junction known to those skilled in the art. The rotary junction may be a one channel rotary junction or a two channel rotary junction.

Alternatively or additionally, in the serial time-encoded 2D imaging system 1700 shown in FIG. 17, the 2D disperser 170 substitutes a SEE probe and the element 108 may be the sample.

In one or more embodiments, a SEE probe may further include a lens located between the DG 104 and the sample or object (e.g., object 130). Preferably, in such an embodiment, the lens receives light from the fiber 102, DG 104 and/or the prism 109 (depending on which system, such as the system 100, the system 1100, the system 1600, the system 1700, etc., includes the lens) and passes the light therethrough towards the sample. After illuminating the sample, the light passes through the lens back towards the DG 104 and/or the prism 109 and into the fiber 103. In one or more embodiments, the lens may or may not be tilted or angled.

In one or more embodiments, the illumination portion of the SEE probe may be separate from the detection portion of the SEE probe. For example, in one or more applications, a probe may refer to the illumination assembly, which includes the illumination fiber 102 (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: the detection fiber 103, the spectrometer 108, the computer 1200, the photodiode 150, etc. The detection fibers, such as the detection fiber(s) 103, may surround the illumination fiber, such as the IF 102, and the detection fibers may or may not be covered by the grating, such as the grating 104.

Unless otherwise discussed herein, like numerals indicate like elements. For example, while variations or differences exist between the systems, such as, but not limited to, the system 100, the system 1100 and the system 1600, the system 1700, etc., one or more features thereof may be the same or similar to each other, such as, but not limited to, the light source 101 or other component(s) thereof (e.g., a photodiode 150, the console 1200, the console 1200', etc.). Those skilled in the art will appreciate that the light source 101, the motor 139, the MCU 140, the spectrometer 108, the at least one detector 107 and/or one or more other elements of the system 100, may operate in the same or similar fashion to those like-numbered elements of one or more other systems, such as, but not limited to, the system 1100, the system 1600, the system 1700, etc. as discussed herein. Those skilled in the art will appreciate that alternative embodiments of the system 100, the system two, the system 1600, the system 1700 and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100, the system 1100, the system 1600 and the system 1700 as discussed herein, there are similarities. Likewise, while the console or computer 1200 may be used in one or more systems (e.g., the system 100, the system 1100, the system 1600, the system 1700, etc.), one or more other consoles or computers, such as the console or computer 1200', may be used additionally or alternatively.

There are many ways to compute intensity, viscosity, speckle detection or any other measurement discussed herein, digital as well as analog. In at least one embodiment, a computer, such as the console or computer 1200, 1200', may be dedicated to control and monitor the SEE devices, systems, methods and/or storage mediums described herein.

Various components of a computer system 1200 (see e.g., the console or computer 1200 as shown in FIG. 1, FIG. 11A, FIG. 16 and FIG. 17) are provided in FIG. 18. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 18). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a SEE device or system, such as, but not limited to, the system 100, the system 1100, the system 1600 and/or the system 1700, discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for SEE tissue characterization, diagnosis, evaluation and imaging. The system 1200 may further include one or more processors connected via a network connection (e.g., via network 1206). The CPU 1201 and any additional processor being used by the system 1200 may be located in the same telecom network or in different telecom networks (e.g., performing SEE technique(s) may be controlled remotely).

The I/O or communication interface 1205 provides communication interfaces to input and output devices, which may include the light source lot, a spectrometer, a microphone, a communication cable and a network (either wired or wireless), a keyboard 1210, a mouse (see e.g., the mouse 1211 as shown in FIG. 19), a touch screen or screen 1209, a light pen and so on. The Monitor interface or screen 1209 provides communication interfaces thereto.

Any methods and/or data of the present disclosure, such as the methods for performing SEE tissue characterization, diagnosis, examination and/or imaging with speckle detection as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 19), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 10. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 10) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip (s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 1200' is shown in FIG. 19. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 1200' includes a display 1209. The computer 1200' may connect with the MCU 140 and the spectrometer 108 via the operation interface 1214 or the network interface 1212. A computer, such as the computer 1200', may include the MCU 140 in one or more embodiments. The operation interface 1214 is connected with an operation unit such as a mouse device 1211, a keyboard 1210 or a touch panel device. The computer 1200' may include two or more of each component.

A computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 1200, 1200', communicates with the MCU 140 to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate a SEE system (e.g., the system 100, the system 1100, the system 1600, etc.). An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs the system (e.g., the system 100, the system 1100, the system 1600, etc.) to set or change the imaging condition, and to start or end the imaging. The laser source 101 and the spectrometer 108 may have interfaces to communicate with the computers 1200, 1200' to send and receive the status information and the control signals.

The present disclosure and/or one or more components of devices, systems and storage mediums, and/or methods, thereof also may be used in conjunction with any suitable optical assembly including, but not limited to, SEE probe technology, such as in U.S. Pat. Nos. 6,341,036; 7,447,408; 7,551,293; 7,796,270; 7,859,679; 7,872,759; 7,889,348; 8,045,177; 8,145,018; 8,289,522; 8,838,213; 8,928,889; 9,254,089; 9,295,391 to Tearney et al. as well as the disclosures in Patent Application Publication Nos. WO2015/116951 and WO2015/116939 and in U.S. Pat. No. 9,332,942 and in U.S. Patent Publication No. 2012/0101374, each of which patents and patent publications are incorporated by reference herein in their entireties.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389; 2012/0101374 and 2016/0228097, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

The invention claimed is:

1. An apparatus for identifying sample type of a sample, comprising:
    a Spectrally Encoded Endoscopy ("SEE") probe including at least a grating and one or more optical fibers;
    a spectrometer;
    a detector that operates to acquire one or more intensities;
    a motor;
    a motion controller that operates to change a speed of the motor; and
    at least one processor that operates to calculate a speckle intensity autocorrelation function and/or process or perform laser speckle imaging (LSI).

2. The apparatus of claim 1, further comprising one or more of:
    a light source;
    a spacer element disposed at a distal end of the SEE probe such that the spacer element and the grating are adjacent and/or connected; and a sheath housing the SEE probe,
wherein the motor includes, is connected to or is a rotary junction that operates to rotate the SEE probe.

3. The apparatus of claim 2, wherein the apparatus is a forward-viewing SEE apparatus.

4. The apparatus of claim 1, wherein the apparatus is a side-viewing SEE apparatus.

5. The apparatus of claim 1, wherein the motor is a stepping motor or a servo motor.

6. The apparatus of claim 2, wherein one or more of: (i) the motion controller stops the motor while the detector acquires the one or more intensities; and (ii) the motion controller changes the speed of the motor while the detector acquires the one or more intensities.

7. The apparatus of claim 6, wherein the motion controller stops the motor at different motor positions at least two times, while the detector acquires the one or more intensities, or changes the speed of the motor at different motor positions at least two times, when the detector acquires intensities.

8. The apparatus of claim 6, wherein the motion controller stops the motor at each motor position in successive scanning, while the detector acquires the one or more intensities.

9. The apparatus of claim 1, further comprising a memory coupled to the at least one processor, the memory operating to store a look-up table including $\beta$ values and decay times calculated by speckle intensity autocorrelation functions, and including the sample type.

10. The apparatus of claim 1, further comprising a display or screen that operates to display a user interface via which an operator or user of the apparatus selections one or more positions, one or more lines or one or more regions of interest from which to obtain the one or more intensities.

11. The apparatus of claim 10, wherein the display or screen further operates to display overlapped images of morphological feature(s) and viscosity or the sample type of the sample being characterized, diagnosed and/or examined.

12. The apparatus of claim 1, further comprising a photodiode optically connected to the grating and connected to the at least one processor, and the photodiode operates to detect one or more time varying speckle intensities separated from the spectrometer.

13. The apparatus of claim 12, wherein one or more of:
a whole range of wavelength or windowed range of wavelength is averaged when the photodiode obtains intensity data;
the photodiode is connected to at least one of the one or more optical fibers through a fiber coupler;
the intensity data obtained by the photodiode is stored in one or more memories;
the stored intensity data obtained by the photodiode is solely used for calculating the speckle intensity autocorrelation function, so that the at least one processor can separate the SEE imaging and sample characterization to stabilize the apparatus; and
the speckle intensity autocorrelation function or functions acquired in each scanning line are more distinguishable for sample characterization, because achievable Hz by the photodiode is higher than when using the detector.

14. The apparatus of claim 1, wherein the one or more optical fibers include: (i) one or more illumination fibers that operate to send light from a light source through the motor and to the grating to illuminate the sample with light; and (ii) one or more detection fibers that operate to receive light reflected from the sample and that passes back through the grating and into the one or more detection fibers.

15. A system for characterizing a sample, the system comprising:
an apparatus for characterizing the sample, the apparatus including:
(i) an interface including a light guiding component, and a motor;
(ii) a spectral encoder including a light focusing component and a light dispersive component; and
(iii) a speckle detector including a motion controller that operates to change a speed of the motor, and one or more processors that operates to calculate a speckle intensity autocorrelation function and/or process or perform laser speckle imaging (LSI);
a light source that operates to send light to the light guiding component of the apparatus for characterizing the sample;
a rotary junction connected to or with the interface of the apparatus; and
a spectrometer including one or more detectors.

16. The system of claim 15, further comprising a sheath having a plurality of tendons therein, the plurality of tendons operating to control motion of the sheath.

17. The system of claim 16, wherein the plurality of tendons comprises four tendons, where two of the four tendons control up-down and down-up movement of the sheath and the other two of the four tendons control left-right and right-left movement of the sheath.

18. A method for characterizing a sample with speckle detection using a Spectrally Encoded Endoscopy ("SEE") system, the method comprising:
forming a SEE image of the sample;
designating at least a partial region or line in the SEE image;
calculating a speckle intensity autocorrelation function to determine a sample type in the designated region or line and/or performing or processing laser speckle imaging (LSI); and
causing a display of the SEE system to display the sample type information together with the SEE image.

19. The method of claim 18, further comprising:
setting sample information;
designating one or more imaging conditions;
starting the imaging or the formation of the SEE image and/or starting reconstruction or formation of the SEE image or images;
coordinating intensities to construct a SEE image;
calculating a g2(t) function to determine the sample type;
displaying the sample type on a center or other predetermined location of a scanned image; and
determining whether to change the line, the partial region or a Region of Interest (ROI) or not.

20. The method of claim 18, further comprising calculating viscosity of the sample using accumulated speckle fluctuations.

* * * * *